United States Patent
Haas et al.

(10) Patent No.: US 6,629,417 B2
(45) Date of Patent: *Oct. 7, 2003

(54) HAND-HELD, HEAT SINK CRYOPROBE, SYSTEM FOR HEAT EXTRACTION THEREOF, AND METHOD THEREFORE

(75) Inventors: Michael Haas, Covington, LA (US); Richard Bailey, Mandeville, LA (US); Jerome F. Krentel, Covington, LA (US)

(73) Assignee: Cimex BioTech, L.C., Covington, LA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/210,861

(22) Filed: Aug. 1, 2002

(65) Prior Publication Data

US 2003/0024250 A1 Feb. 6, 2003

Related U.S. Application Data

(63) Continuation-in-part of application No. 09/858,083, filed on May 15, 2001, now Pat. No. 6,430,956.

(51) Int. Cl.[7] .............................. F25D 3/00; F25B 21/00
(52) U.S. Cl. ............................................. 62/3.2; 62/293
(58) Field of Search ........................... 62/293, 3.2, 3.7, 62/6; 607/113

(56) References Cited

U.S. PATENT DOCUMENTS

| | | |
|---|---|---|
| 3,451,395 A | 6/1969 | Thyberg |
| 3,502,080 A | 3/1970 | Hirschhorn |
| 3,668,888 A | 6/1972 | Roslonski |
| 4,037,631 A | 7/1977 | Schulze et al. |
| 4,206,609 A * | 6/1980 | Durenec ........................ 62/6 |

(List continued on next page.)

OTHER PUBLICATIONS

A Study of Safety and Performance Requirements for Cryosurgical Devices, NTIS PB81124930 ECRI Plymouth Meeting, PA 1980.

Cryosurgery for Common Skin Lesions, Canadian Family Physician, vol. 45, Apr. 1999 pp. 964–974.

Rubinsky, Boris, Cryosurgery, Annu Rev Biomed Eng 2000 02:157–87.

Histofreezer brochure, Item 10206 04/00 (2 pages).

Brymill Cryogenic Systems Brochure (3 pages) no date.

(List continued on next page.)

*Primary Examiner*—William C. Doerrler
(74) *Attorney, Agent, or Firm*—Joseph T Regard, Ltd

(57) ABSTRACT

A cryoprobe system utilizing a monolithic, insulated, hand-held thermal mass having an exposed tip for cryosurgical applications and the like, as well as a heat extraction base configured to interface with the thermal mass to quickly and efficiently reduce the heat of the thermal mass to cryogenic temperatures. The heat extraction base of the preferred embodiment of the present invention is configured to interface with the tip of the thermal mass, such that the tip plugs in securely to the base, to permit an efficient thermal transfer of heat from the thermal mass through the base via a heat exchange system communicating with the base which employs a low temperature cryo-refrigeration unit. The cryo-refrigeration unit may comprise a single low temperature cooling unit to reduce the temperature of the base to around minus one hundred degrees Centigrade utilizing off-the-shelf cryogenic refrigeration methods, or may utilize a series of more conventional refrigeration units in a primary and secondary heat extraction arrangement, which method may further utilize thermocouple or Peltier effect device assist to further reduce the temperature of the heat extraction base to the required temperature. Also claimed is the method of cryosurgery employing the device(s) of the present invention, and a heat pipe appliance to engage a remote treatment area.

24 Claims, 16 Drawing Sheets

U.S. PATENT DOCUMENTS

| | | | |
|---|---|---|---|
| 4,519,389 A | | 5/1985 | Gudkin et al. |
| 5,132,089 A | | 7/1992 | Lightfoot |
| 5,207,674 A | | 5/1993 | Hamilton |
| 5,277,030 A | * | 1/1994 | Miller .......................... 62/3.2 |
| 5,603,221 A | * | 2/1997 | Maytal ....................... 62/51.2 |
| 5,758,505 A | | 6/1998 | Dobak, III |
| 5,910,104 A | | 6/1999 | Dobak, III |
| 5,992,158 A | | 11/1999 | Goddard et al. |
| 6,017,337 A | | 1/2000 | Pira |
| 6,035,657 A | | 3/2000 | Dobak, III |
| 6,096,032 A | | 8/2000 | Rowland |
| 6,126,684 A | * | 10/2000 | Gobin et al. ................ 607/113 |
| 6,151,901 A | | 11/2000 | Dobak, III |
| 6,182,666 B1 | | 2/2001 | Dobak, III |
| 6,193,644 B1 | | 2/2001 | Dobak, III et al. |
| 6,237,355 B1 | | 5/2001 | Li |
| 6,270,494 B1 | | 8/2001 | Kovalcheck et al. |
| 6,364,899 B1 | * | 4/2002 | Dobak, III .................. 607/113 |
| 6,430,956 B1 | * | 8/2002 | Haas et al. ................... 62/293 |

OTHER PUBLICATIONS

Family Practice Cryosurgery page with pic of Wallach LL–100 device (4 pages) No date.

Wallach Surgical Devices, Inc. pages entitled Ultrafreeze Liquid Nitrogen Cryosurgical System (2 Pages) (C) 1998, HPV Tips (1 Page), (C) 1991.

Holman, MR, Roland, SJ, Design and Development of a New Cryosurgical Instrument Utilizing Peltier Thermoelectric Effect, Jrnl Med Eng & Tech. vol. 21, No. 3–4, May–Aug. 97, pp. 106–110.

Hamilton, A, Hu, J, An Electronic Cryoprobe for Cryosurgery Using Heat PPES and Thermoelectric Coolers; Jrnl Med Eng & Tech, vol. 17, No. 3, May–Jun. 1993 pp. 104–109.

Global Coolling web pabe http://www.globalcooling.com/stircoolunit.html dated accessed Dec. 28, 2000 entitled Free Piston Stirling Cooler, (3 pages), and http://www.globalcooling.com/m100–specs.html (1 page).

Analog Devices brochure on AD596/AD597 Thermocouple Conditioner and setpoint controller (C) 1998 (8 pages).

Revco, on–line Catalog dated May 13, 2001 entitled "Ultima II Series Ultra Low Temperature Freezers", 6 Pages at http://www.revoc-sci.com/catalog/ult/ult_ultima2.htm.

Revco on–line Catalog dated May 13, 2001 page "New Refrigeration Technology" at http://www.revoc–sci.com/catalog/ult/ult_tech.htm (1 page).

Revco on–line catalog dated May 13, 2001 LEGACI schematic dated May 13, 2001 at http://www.revoc–sci.com/catalog/ult/ult_tech.htm (2 pages).

Revco on–line catalog dated May 13, 2001 LEGACI Value Series Ultra Low Temperature Freezers at http://www.revoc-sci.com/catalog/ult/ult_value.htm (5 pages).

Berchowitz, David, McEntee, Jarlath, Welty, Steven; "Design and testing of a 40 W Free–Piston Stirling Cycle Cooling Unit"; 20th International Congress of Refrigeration, IIR/IIF, Sidney 1999(7 pages).

* cited by examiner

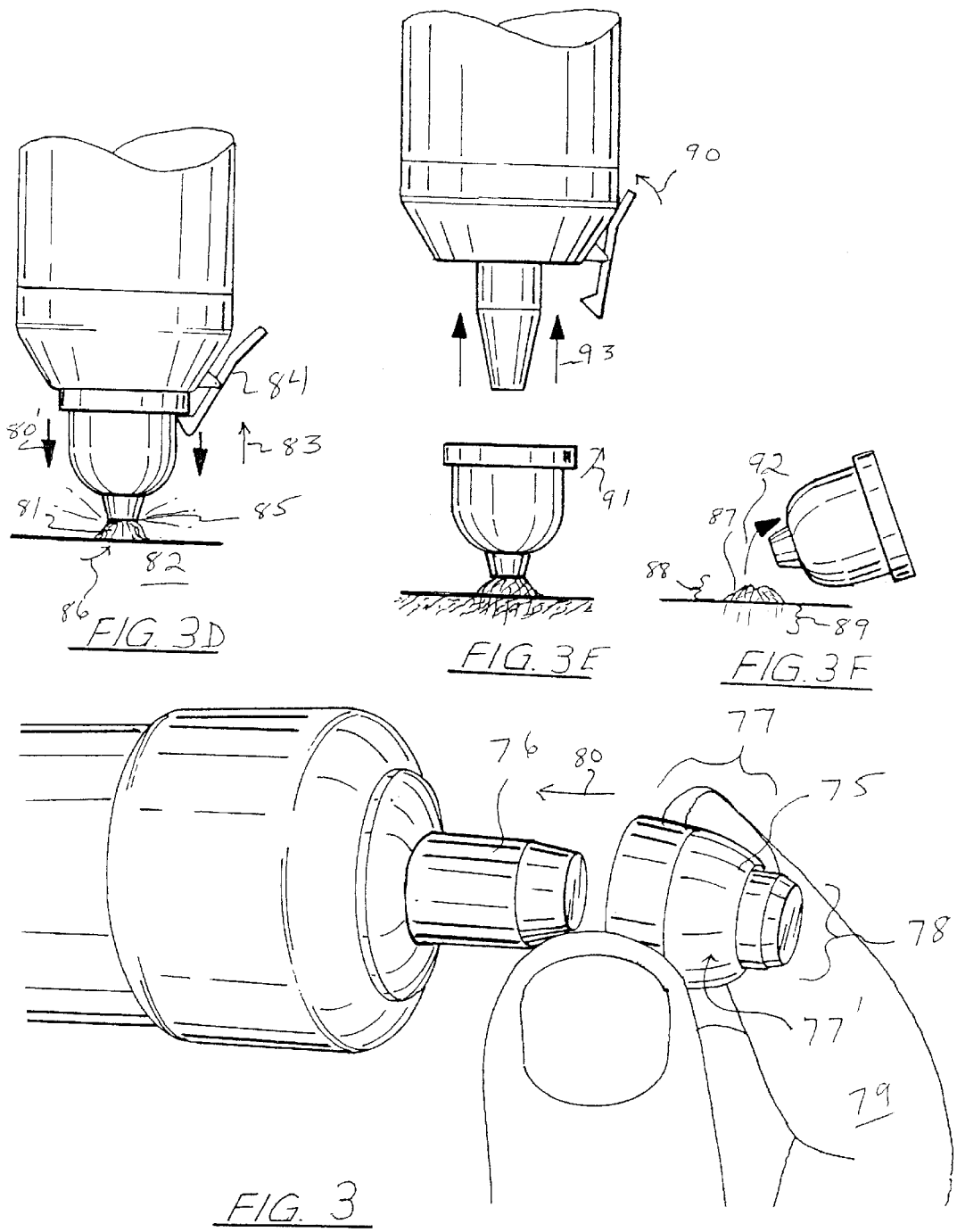

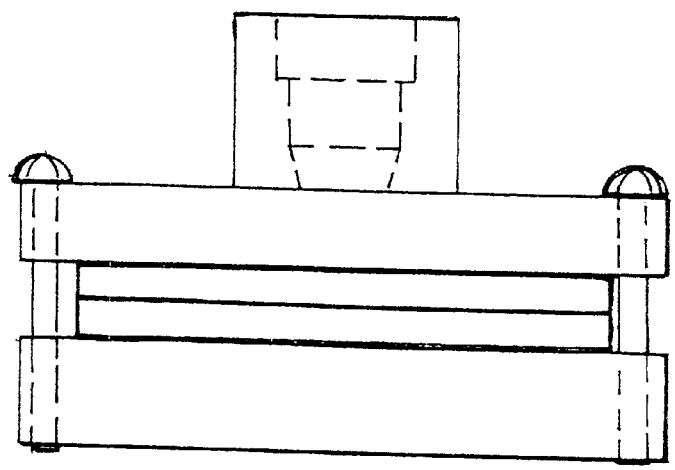
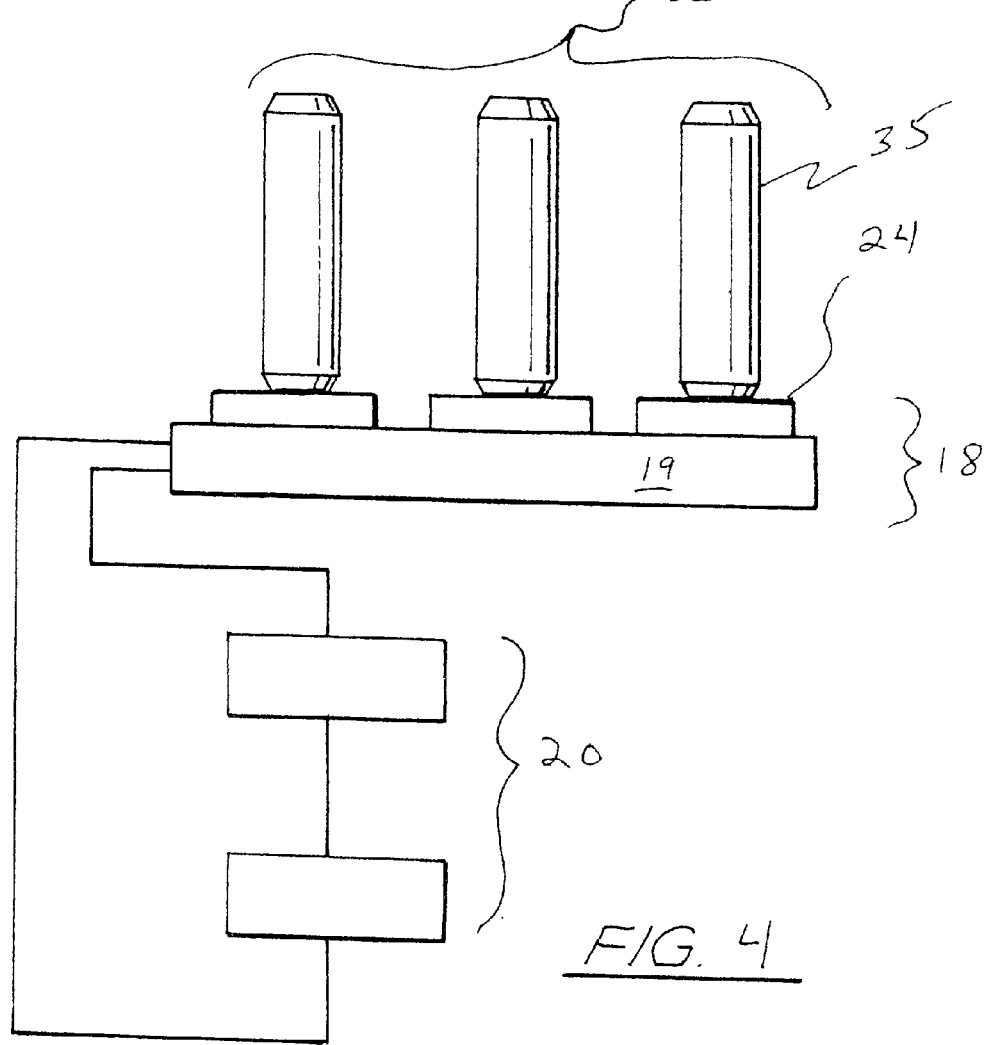
FIG. 4B
FIG. 4

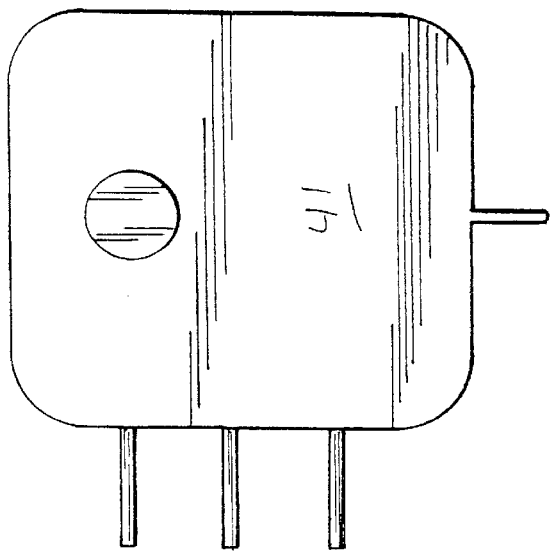
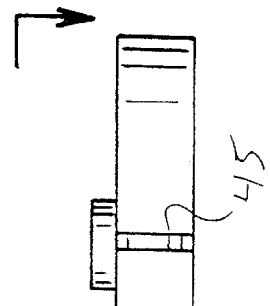
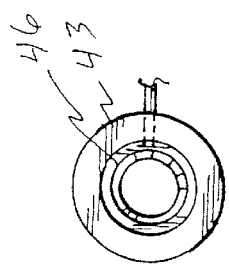
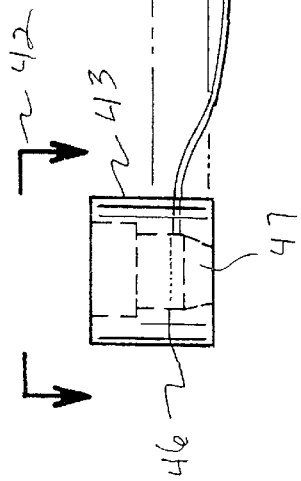
FIG. 5A
FIG. 5B
FIG. 5

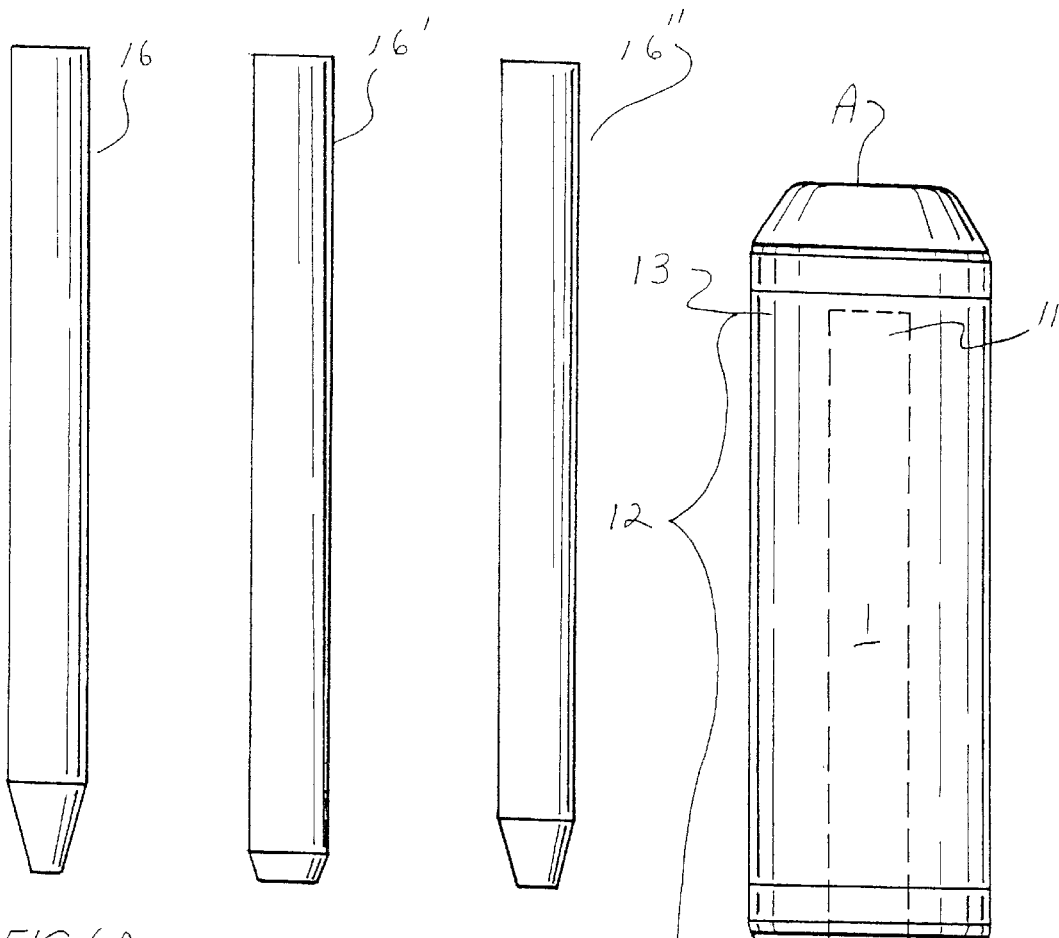

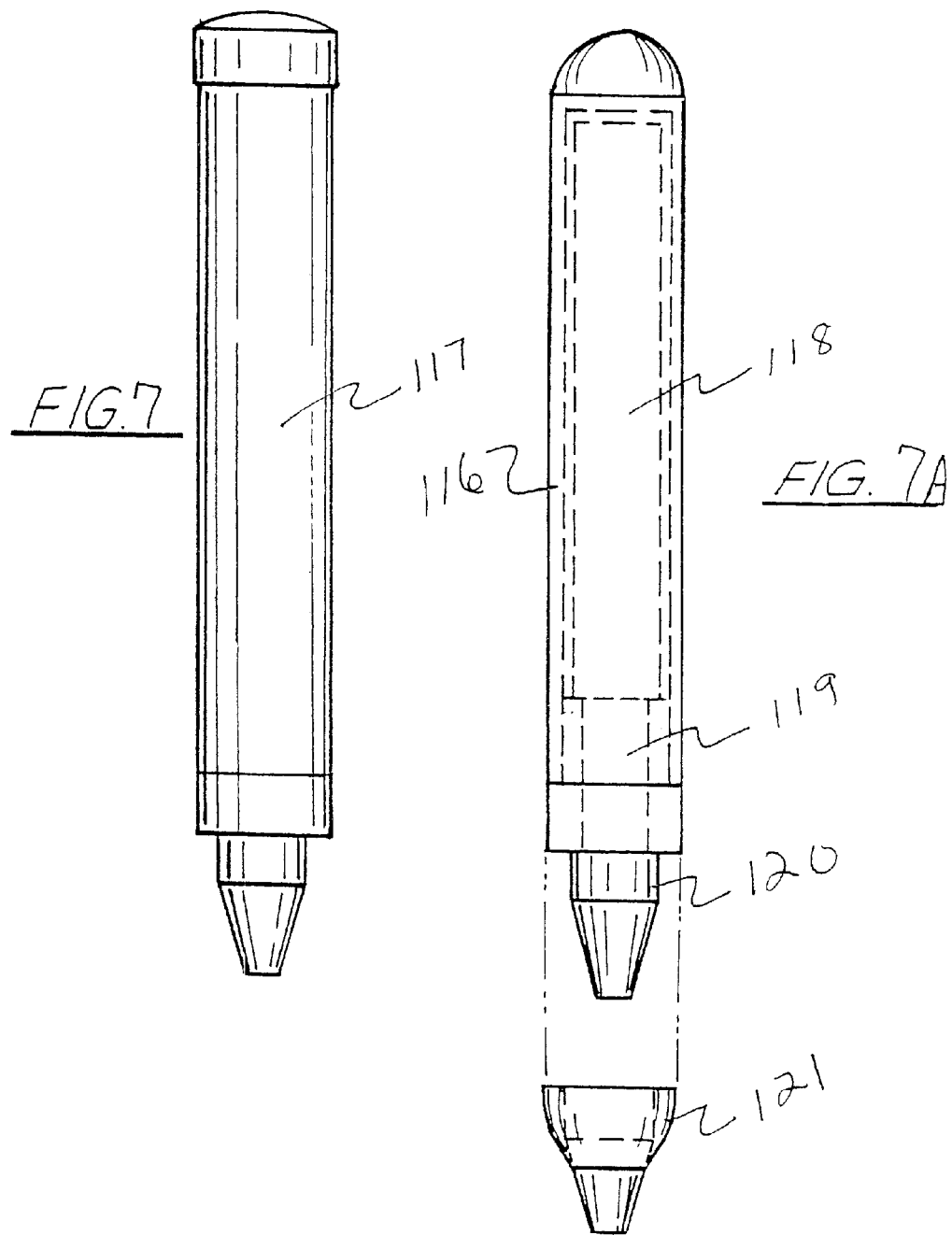

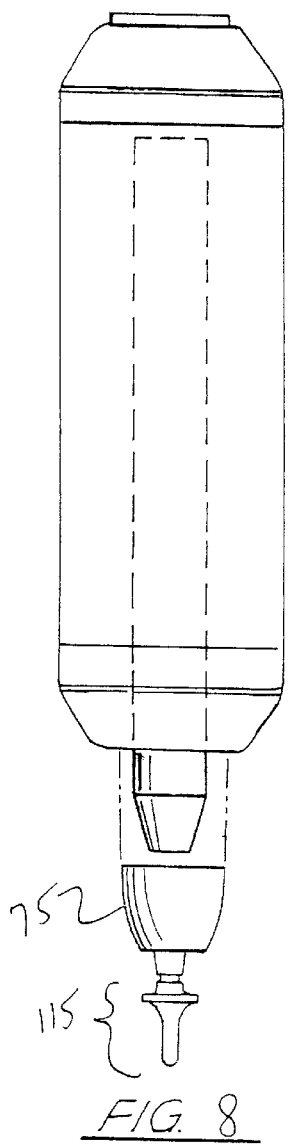
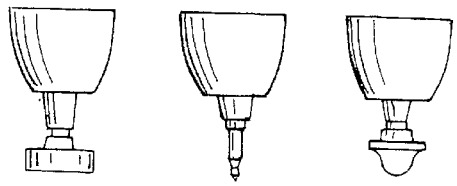
FIG. 8C  FIG. 8D  FIG. 8E
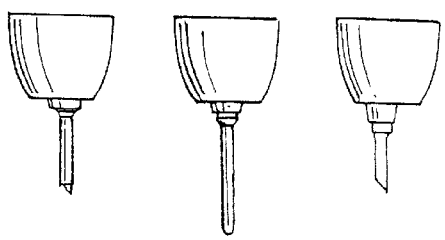
FIG. 8F  FIG. 8G  FIG. 8H
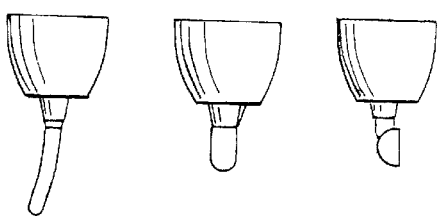
FIG. 8I  FIG. 8J  FIG. 8K
FIG. 8
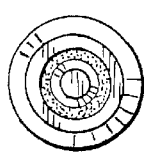
FIG. 8A
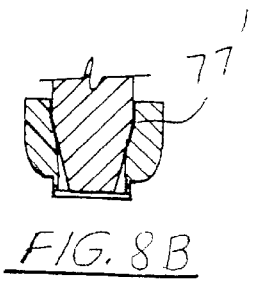
FIG. 8B

HAND-HELD, HEAT SINK CRYOPROBE, SYSTEM FOR HEAT EXTRACTION THEREOF, AND METHOD THEREFORE

STATEMENT OF CONTINUING APPLICATION

The present application is a continuation-in-part of U.S. patent application Ser. No. 09/858,083, filed May 15, 2001, now U.S. Pat. No. 6,430,956 entitled "Hand-Held, Heat Sink Cryoprobe, System for Heat Extraction Thereof, and Method Therefore".

TECHNICAL FIELD OF THE INVENTION

The present invention relates to cryosurgical probes, and in particular to a cryoprobe system utilizing a passive, insulated, hand-held thermal mass having a low temperature tip for cryosurgical medical applications and the like, as well as a heat extraction base configured to interface with the thermal mass to quickly and efficiently reduce the heat of the thermal mass to cryogenic temperatures.

The heat extraction base of the preferred embodiment of the present invention is configured to interface with the tip of the thermal mass, such that the tip plugs in securely to the base, to permit an efficient thermal transfer of heat from the thermal mass through the base via a heat exchange system communicating with the base which employs a low temperature cryo-refrigeration unit.

The cryo-refrigeration unit may comprise a single low temperature compressor to reduce the temperature of the base to around minus one hundred degrees Centigrade utilizing off-the-shelf cryogenic refrigeration methods, or may utilize a series of more conventional refrigeration units in a primary and secondary heat extraction arrangement, which method may further utilize thermocouple or Peltier effect device assist to further reduce the temperature of the heat extraction base to the required temperature.

The thermal mass is configured to be cooled to an optimal temperature for cryogenic applications, removed from the base, the tip of the otherwise insulated thermal mass then applied to the surface to be treated, typically tissue on a patient, wherein the cooled thermal mass provides a heat sink via the tip to cryogenically cool the treated surface.

The present invention also contemplates utilization of a heat pipe attachment for Endo-Cervical Cryogenic Treatment, which heat pipe has first and second ends, the first end configured to engage the tip of the thermal mass, the second end configured to engage remote tissue of a patient (i.e., the cervix) for cryogenic treatment of same. The length of the heat pipe may be insulated, with the treatment end (the second end) exposed or engaging a specially configured thermal application tip.

BACKGROUND OF THE INVENTION

Cryosurgery, or cryo-ablation, employs the technique of destructively freezing, or ablating, targeted biological tissue to destroy same. A large array of systems for cryosurgery have been developed since its inception utilizing low and high pressure cryogenic liquid refrigerants, closed refrigeration systems, to solid state thermoelectric devices.

By far the most common method of performing cryosurgery involves the utilization of fluids having a low boiling point, either applied directly to the tissue of the patient or utilized to cool a probe or applicator tip. Liquid Nitrogen, Nitrous Oxide, Carbon Dioxide, or aerosol (Histofreezer) comprise the most widely used cryosurgical modalities currently in use of this type.

Liquid nitrogen has been widely utilized for cryosurgery since the 1940's, when it became more readily available. In low pressure applications, typically a Dewar-type storage flask is required to store the liquid, which must be replenished on a regular basis. The physician may spray the liquid on the tissue to be applied, or may dip a cotton swab or the like into the liquid nitrogen to absorb said liquid, thereafter applying the swab to the portion to be treated.

While Liquid Nitrogen has a boiling point of −196 degrees Centigrade, when employed in cryosurgery, erratic temperatures can arise. For example, when dabbed on with a cotton swab, skin surface temperatures can be as high as −0 degrees Centigrade, but can go as low as −100 degrees Centigrade if a continuous flow of LN2 is applied to the skin rapidly.

Alternatively, a probe having a tip configured to conform to the anatomy to be applied may be chilled to cryogenic temperatures by the liquid, flowing therethrough, and allowing same to boil to adsorb heat, allowing the tip to act as a heat sink. Utilization of such a probe is preferred in gynecologic, oral, rectal, or other invasive applications, where the probe can be formed to conform with the anatomy to which it is applied. As the evaporation of the fluid is the principle behind its cooling properties, an emission of the gas occurs in the area in which it is employed.

Nonetheless, liquid Nitrogen provides the most effective, widely utilized cryogen fluid, having a low boiling point of −196 degrees Centigrade. This low temperature in and of itself provides risks, due to possible over application and associated over freezing, as well as risks of spills, and possible splattering during handling, as even indirect contact to tissue can result in tissue damage. Protective eyewear, clothing, and gloves are therefore required, and the material must be stored and administered under Federal OSHA guidelines.

Nitrous Oxide and Carbon Dioxide are similarly used, but are stored in a pressurized tanks, so they have the benefit of not being depleted during storage. However, studies have shown that Nitrous Oxide can be harmful to a Fetus, and breathing Nitrous Oxide can result in reduced fertility in females. Further, liquid Nitrous Oxide boils at a higher temperature (−89 degrees Centigrade) than Nitrogen, which can result in a less effective treatment. Carbon dioxide when evaporated displaces oxygen in the treatment area, and has even a higher boiler point (−78 degrees Centigrade) than Nitrous Oxide, which makes it far less suitable as a refrigerant. Nitrous oxide can employ a J-T expansion tip to reach tip temperatures down to about −89 degrees centigrade, and is favored as a reliable temperature delivery system, but suffers as its downside the above mentioned health risks.

HISTOFREEZE is a liquid refrigerant formulation comprising an aerosol which may be dispensed to a cotton swab or other application tip via an aerosol can. However, the refrigerant has a much higher boiling point than nitrogen, resulting in less cooling to the tissue (about −2 degrees Centigrade) to be treated, and is thereby far less effective. Like the above refrigerants, the aerosol evaporates into the atmosphere of the treatment area which can be breathed by its occupants, unless it is vented.

The liquid nature of the above refrigerants makes it very difficult to precisely cool the treated area to an exact temperature, resulting in the tissue often being undercooled or overcooled. While the degree of cooling varies with the type of tissue and depth and type of abnormality, the area should generally be exposed to at least −20 degrees Centigrade, and ideally −50 degrees centigrade to effectively treat malignant tissue.

In addition to the above methods, cryosurgical treatment devices utilizing self contained cooling apparatus have also been employed, but these units have often proved expensive, cumbersome and difficult to use, while rarely providing the cooling effectiveness of liquid nitrogen. Accordingly, such devices have not been employed in any significant extent compared with the above systems.

A list of patents which may have some pertinence to the present invention include:

| U.S. Pat. No. | Inventor | Date of Issue |
| --- | --- | --- |
| 5132089 | Lightfoot | Jul. 21, 1992 |
| 4037631 | Schulze et al | Jul. 26, 1977 |
| 4519389 | Gudkin et al | May 28, 1985 |
| 5207674 | Hamilton | May 4, 1993 |
| 3502080 | Hirschhorn | Mar. 24, 1970 |
| 3668888 | Roslonski | Jun. 13, 1972 |
| 3451395 | Thyberg | Jun. 24, 1969 |
| 5992158 | Goddard et al | Nov. 30, 1999 |
| 3575176 | Crump | Apr. 20, 1971 |
| 6096032 | Rowland | Aug. 1, 2000 |

U.S. Pat. No. 5,132,089 to Lightfoot teaches a "Hand-Held Cryofixation Apparatus" wherein "a metal block is precooled by immersion into a cryogen such as liquid nitrogen or helium."

U.S. Pat. No. 4,037,631 to Schulze et al teaches a "Method of Charging a Cryogenic probe" wherein a probe is inserted in a cryogenic liquid container (FIG. 4–7).

U.S. Pat. No. 3,502,080 and 4,519,389 teach diverse cryogen probes having application tips which are cooled via thermocouple or Peltier effect devices.

U.S. Pat. No. 3,668,888 teaches a "device for frosting drinking glasses" wherein heat is extracted from a glass via a cooling device which releases refrigerant into the glass to evaporatively cool same.

U.S. Pat. No. 3,451,395 to Thyberg teaches a cryosurgical instrument wherein the probe tip is cooled via cryogenic fluid, which is allowed to boil in the tip via an air vent, so as to extract heat from the tip to cryogenically cool same.

U.S. Pat. No. 3,575,176 teaches a "Rechargeable Cryo-surgical Instrument" having a refrigerant receiving chamber, and a tip which would receive the refrigerant, which tip would be exposed to the atmosphere to allow evaporation of the refrigerant so as to cool same. See also U.S. Pat. No. 3,451,395 for a device of similar operation but different configuration.

U.S. Pat. No. 6,096,032 issued 08/01/2000 teaches a "Micro Cryo-Surgical Device" wherein there is provided a thermoelectric device configured to engage and remove heat from a brass cooling block, the block mounted on to the neck of a Dewar flask containing a coolant, illustrated as a ethylene glycol/water mixture. The cooling block has passages formed therethrough for the passage of the coolant, wherein heat is extracted from same via the thermoelectric device; the coolant is then directed to a second thermoelectric device which interfaces with a copper application tip. The second thermoelectric device, with heat extracted by the coolant, further cools the copper application tip so that it may be utilized in cryogenic surgery applications.

It is anticipated that the '032 device, utilizing conventional thermoelectric devices, would be incapable of extracting sufficient heat from the application tip to provide the heat removal necessary for most cryogenic surgery applications.

Thus, there would appear that the prior art has yet failed to provide a cryogenic device which does not require the use of liquid nitrogen or the like, and instead relying upon closed refrigeration cycles to develop sufficient heat removal from the application tip in an relatively cost effective, easily implemented, and reliable fashion.

GENERAL SUMMARY DISCUSSION OF THE INVENTION

Unlike the prior art, the present invention is believed to provide a system and method for cryosurgery which is safe to use, reliable in operation, cost effective to implement and maintain, and straightforward in use.

In cryosurgery treatment of diseased tissues, the most critical factor is the safe, controlled, freezing of the tissue to the desired, acceptable tissue range. To date the prior art has provide systems wherein it is difficult to gauge the effective freezing of diseased tissues; too often the tissues are overcooled, destroying surrounding tissues, or undercooled, resulting in ineffective treatment. Cell destruction typically starts at about −10 degrees Centigrade to −20 degrees Centigrade, but usually −40 degrees Centigrade to −50 degrees Centigrade is preferable, as this better assures cell destruction.

The preferred embodiment of the present invention comprises two primary components, a hand-held cryogen applicator, comprising an insulated thermal mass having an exposed end which is configured to engage an application tip, and a thermal cooling unit which includes a base having a socket configured to engage said exposed end of the thermal mass, so as to remove heat from said thermal mass to cool same to cryogenic temperatures.

The first working embodiment of the present invention utilizes first and second, cascaded Rankine-cycle cooling systems, driven by a motor-compressor to extract heat from a cold plate by circulating coolant therethrough; further, a thermoelectric device (TMD) is sandwiched between the cooling unit base and the cold plate, with the cold side engaging the base, such that heat extracted from said base, and through said TMD via said cold plate, to bring the temperature down still further. A self-filling solution of antifreeze liquid in the form of purified ethanol alcohol is provided in the socket so as to facilitate more efficient removal of heat from the application tip and thermal mass, as well as displace air and the moisture present therein. A working prototype of this system has successfully chilled the thermal mass and application tip to about −100 degrees Centigrade.

The super-cooled thermal mass can then be removed from the thermal cooling unit, fitted with an application tip to the exposed end, and be utilized as a heat sink to cryogenically cool (i.e., remove heat from), via the application tip, the selected tissue.

In the working prototype of the present invention, there are three different sized cryogen applicators, comprising different sized thermal masses, a smaller unit for treating smaller tissue areas such as moles or the like, a medium sized unit, and a larger mass unit, which provides greater heat sink capability, as may be required for larger or more intense applications, such as may be required in gynecological treatments.

The larger the area, the lower the temperature of the tissue that can be achieved, assuming a specific starting temperature. A numeric temperature display is preferably provided on each cryogen applicator so as to accurately and readily indicate to the user the operational condition of the unit in real time. In the first working prototype, the thermal cooling unit included three sockets to simultaneously engage three cryogen applicators, which can be of similar or disparate sizes; when one applicator in use falls below its optimal temperature range, the tip may be removed, the unit plugged into a socket of the thermal cooling for heat removal, and another cryogen applicator removed from one of the other sockets, which applicator has been sufficiently cooled for immediate use.

An alternative embodiment of the present invention utilizes a Stirling-type refrigerant compressor utilizing helium as the refrigerant, which unit may be as small as a soda can, to quickly, efficiently, and quietly form the cooling means for the thermal cooling unit. This alternative unit dispenses with the need of the cascaded, conventional refrigeration systems and thermoelectric device secondary cooler, and provides a smaller, albeit more expensive, footprint than the present working embodiment of the invention.

It is reiterated that the cooling mechanisms employed in the thermal cooler component of the invention can vary from the above, and may further include liquid nitrogen cooling of the cold plate, magnetic coolers, ultrasonic or laser cooling apparatus, diverse evaporative cooling systems, high grade Peltier effect coolers (which may be stacked).

The thermal mass forming the thermal application of the first working prototype comprised a copper cylinder of solid copper, but there are other suitable materials which could include, for example, Aluminum, Brass, ceramics, thermal gels, etc.

An alterative application system for the present invention is provided in the form of a heat pipe attachment, which heat pipe has first and second ends, the first end configured to (preferably removeably) engage the tip of the thermal mass, the second end configured to interface with isolated tissue in or on a patient (i.e., the cervix) for cryogenic treatment of same. Ideally, the length of the heat pipe is insulated, with the treatment end (the second end) exposed or engaging a specially configured thermal application tip.

It is therefore an object of the present invention to provide a cryosurgical device which includes a hand held applicator unit which is relatively lightweight, compact, and easily utilized, and which is sufficiently chilled so as to provide optimal cryosurgical applications.

It is another object of the present invention to provide a cryosurgical system comprising a thermo-cooling base unit configured to interface with and quickly and effectively super-cool a hand held cryogen applicator unit.

It is another object of the present invention to provide a cryosurgical system comprising a cryogen applicator unit comprising an insulated thermal mass having an exposed end configured to engage diverse application tips, said applicator unit having temperature indicator means.

It is another object of the present invention to provide a cryosurgical system comprising a thermo-cooling base unit comprising cascaded Rankine process refrigeration units configured to super-cool a cold plate, said cold plate having situated thereupon a thermoelectric device engaging at its cold side a socket configured to engage said exposed end of said cryogen applicator unit.

It is another object of the present invention to provide a cryosurgical system comprising a base thermo-cooling station for removably super-cooling a hand manipulable thermal mass, said base station including a socket for receiving an exposed end of said thermal mass, and means for providing liquid antifreeze in said socket so as to prevent any air gaps between said exposed end and said socket when engaged.

Lastly, it is an object of the present invention to provide a system for treating an isolated area of a patient, utilizing a heatpipe having first and second ends, the first end engaging a chilled thermal mass, the second end forming an application area for engaging the treatment area on the patient.

Lastly, it is an object of the present invention to provide a method and system for cryo-ablation of biological tissue utilizing a super-chilled, hand-held thermal mass and separate thermal cooling base station.

BRIEF DESCRIPTION OF DRAWINGS

For a further understanding of the nature and objects of the present invention, reference should be had to the following detailed description, taken in conjunction with the accompanying drawings, in which like parts are given like reference numerals, and wherein:

FIG. 3 is an isometric, close-up view of an application tip being applied to the exposed end of the applicator.

FIG. 3D is a side, close up view of the invention of FIG. 3, illustrating an applicator with application tip applied to a tissue treatment area on a patient.

FIG. 3E is a side view of the invention of FIG. 3D, illustrating the removal of the applicator from the treatment area, leaving the application tip in contact with the treatment area.

FIG. 3F is a side view of the invention of FIG. 3E, illustrating the removal of the application tip from the treated treatment area.

FIG. 4 is a side, partial view of the system of FIG. 1, illustrating cold plate having three modular applicator chilling sockets situated thereon, further illustrating in boxes first and second, cascaded Rankine cycle refrigeration units interfacing with said cold plate to chill same.

FIG. 4B is an end view of the device of FIG. 4A, illustrating in phantom the configuration of an end socket.

FIG. 5 is a side view of an exemplary gravity tank and conveyor tube arrangement to provide a self-filling means for providing a predetermined level antifreeze fluid to each socket of FIG. 4A.

FIG. 5A is a top view of the gravity tank of FIG. 5.

FIG. 5B is a top view of a self-filling socket arrangement of FIG. 5.

FIG. 6 illustrates a side view of the working, preferred embodiment of the applicator of FIG. 2, illustrating in phantom the configuration of the insulated portion of the thermal mass.

FIGS. 6A and 6B illustrate side and end views, respectively, of a thermal mass having a first exposed end configuration, respectively.

FIGS. 6C and 6D illustrate side and end views, respectively, of a thermal mass having a second exposed end configuration.

FIGS. 6E and 6F illustrate side and end views, respectively of a thermal mass having a third exposed end configuration.

FIG. 7 illustrates a side view of a second embodiment of the applicator of FIG. 6, wherein a vacuum insulation jacket is shown.

FIG. 7A is a side view of the applicator of FIG. 7, illustrating in phantom components forming the vacuum insulation jacket and insulated thermal mass, and further illustrating an exemplary application tip.

FIG. 8 illustrates an applicator having fitted thereupon an exemplary applicator tip.

FIG. 8A is an end view of the applicator and tip of FIG. 8.

FIG. 8B is cross-sectional, partial view of the exposed end of the applicator of FIG. 8 having a tip base situated thereupon.

FIGS. 8C, 8D, 8E, 8F, 8G, 8H, 8I, 8J, 8K are side views of various applicator tip configurations for use with the applicator of FIG. 2 or FIG. 7.

DETAILED DISCUSSION OF THE INVENTION

Figure 1:
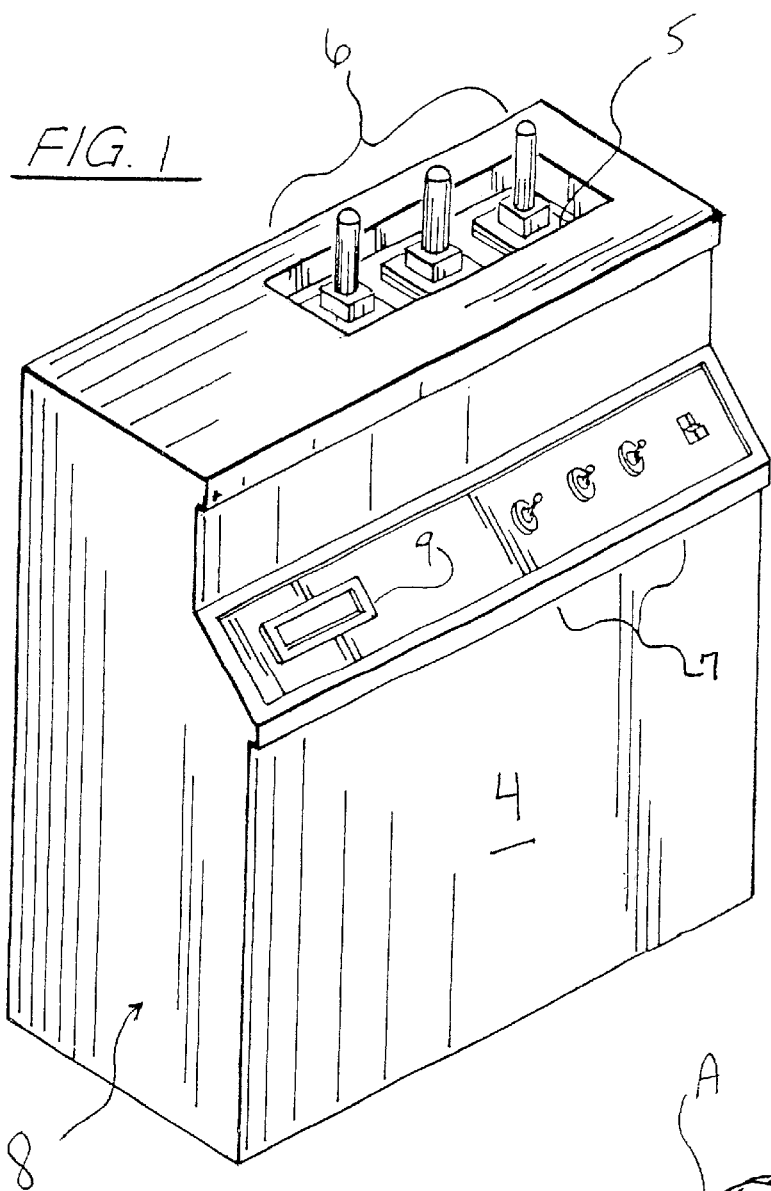
FIG. 1 is an isometric view of the preferred, working system of the present invention, illustrating the cooling unit cooling three hand-held cryogen applicators.
Figure 2:
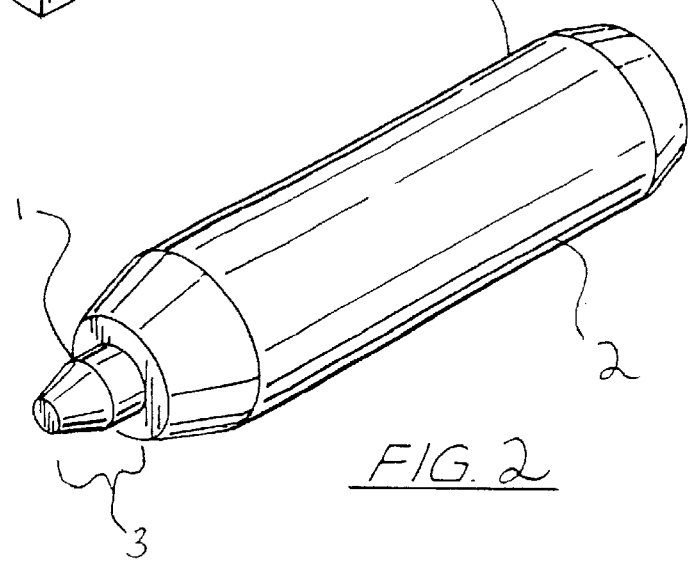
FIG. 2 is an isometric view of a preferred, working embodiment of a hand-held cryogen applicator.
Figure 3A:
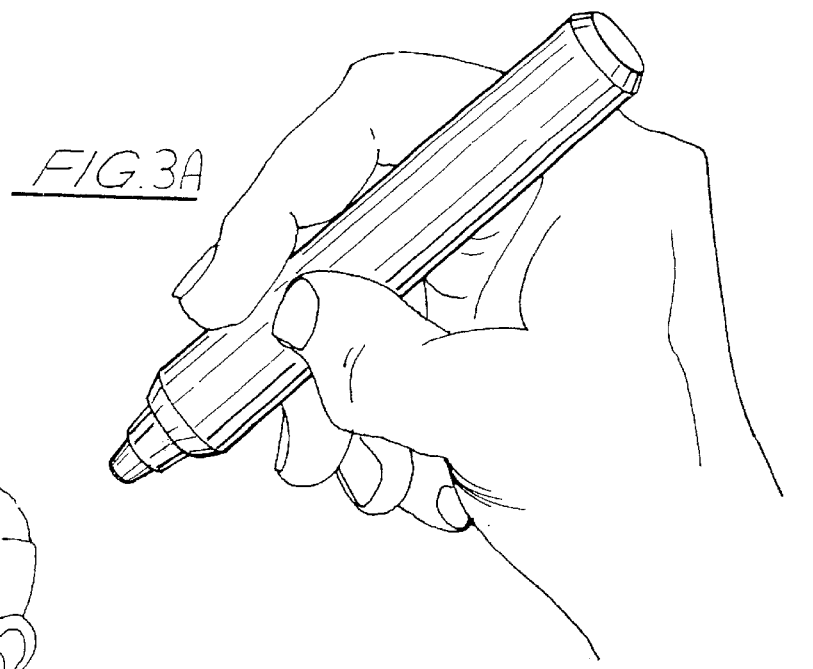
FIG. 3A is an isometric view of the applicator of FIG. 2, as held by an exemplary user.
Figure 3B:
FIG. 3B is an isometric view of the applicator of FIG. 3A being applied to a patient.
Figure 3C:
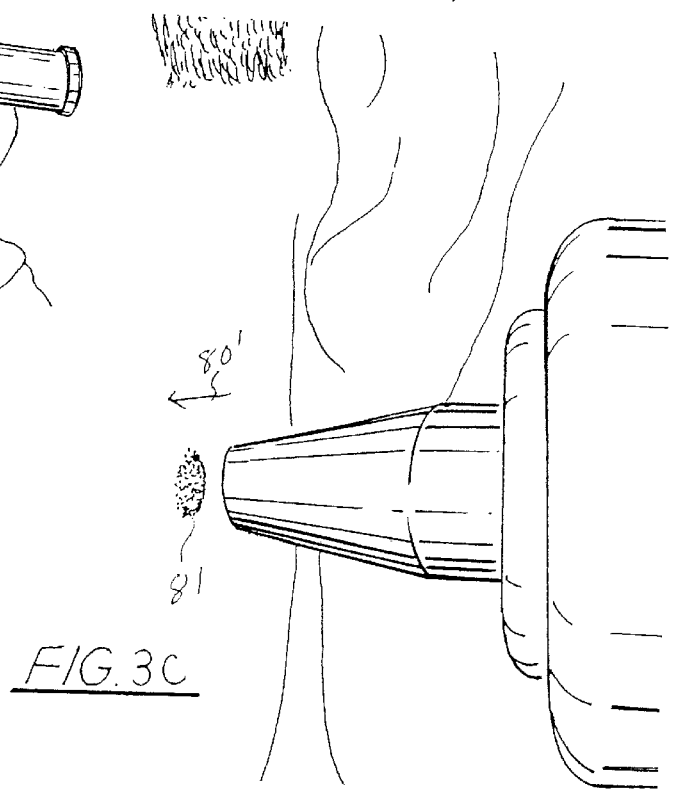
FIG. 3C is a close-up view of FIG. 3B, illustrating the tip of the applicator being applied to a treatment area.
Figure 4A:
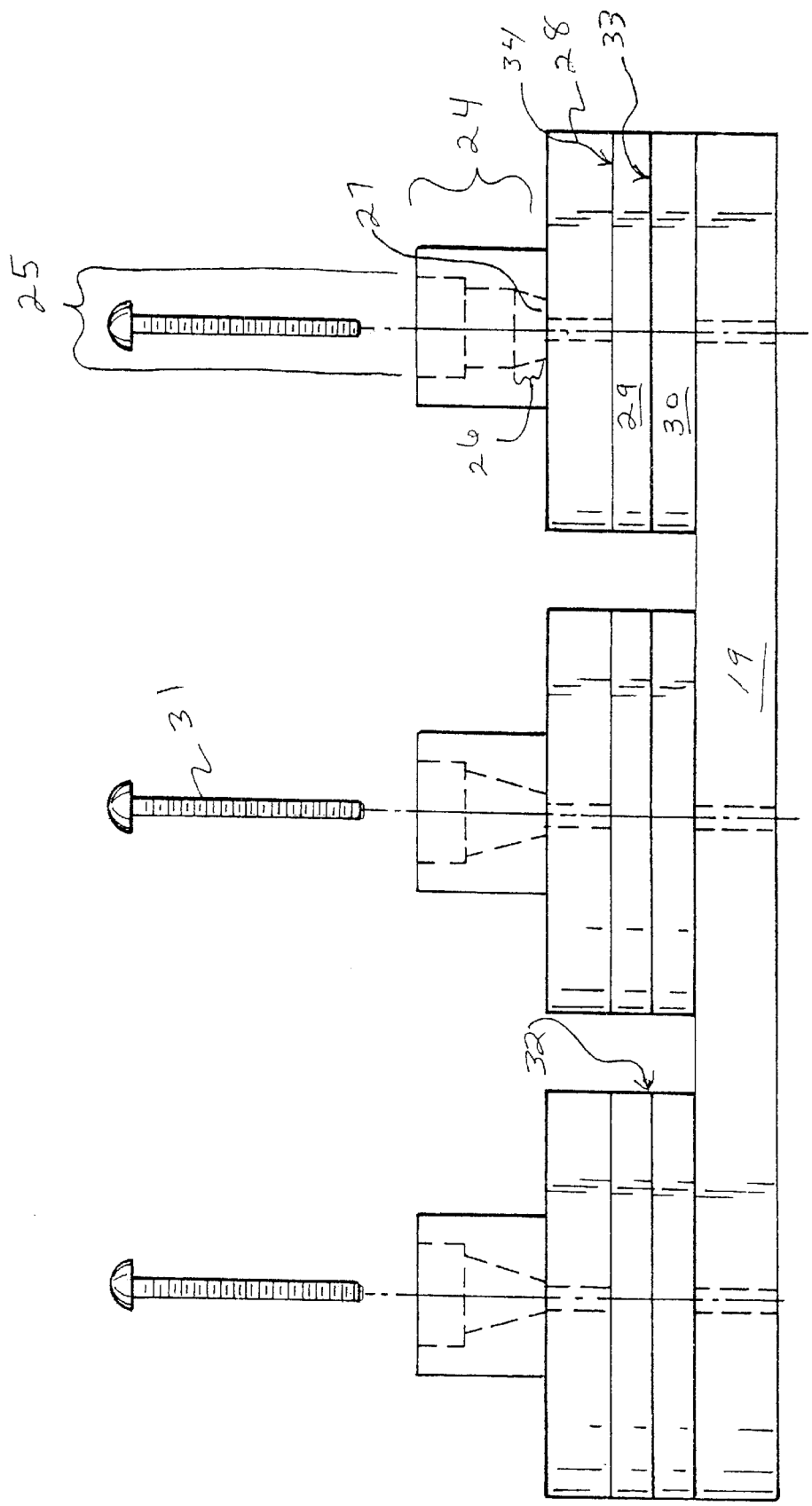
FIG. 4A is a side, close-up view of the cold plate and three modular applicator chilling sockets of FIG. 4, illustrating in phantom the configuration of the sockets to engage the exposed end of the applicators.
Figure 4C:
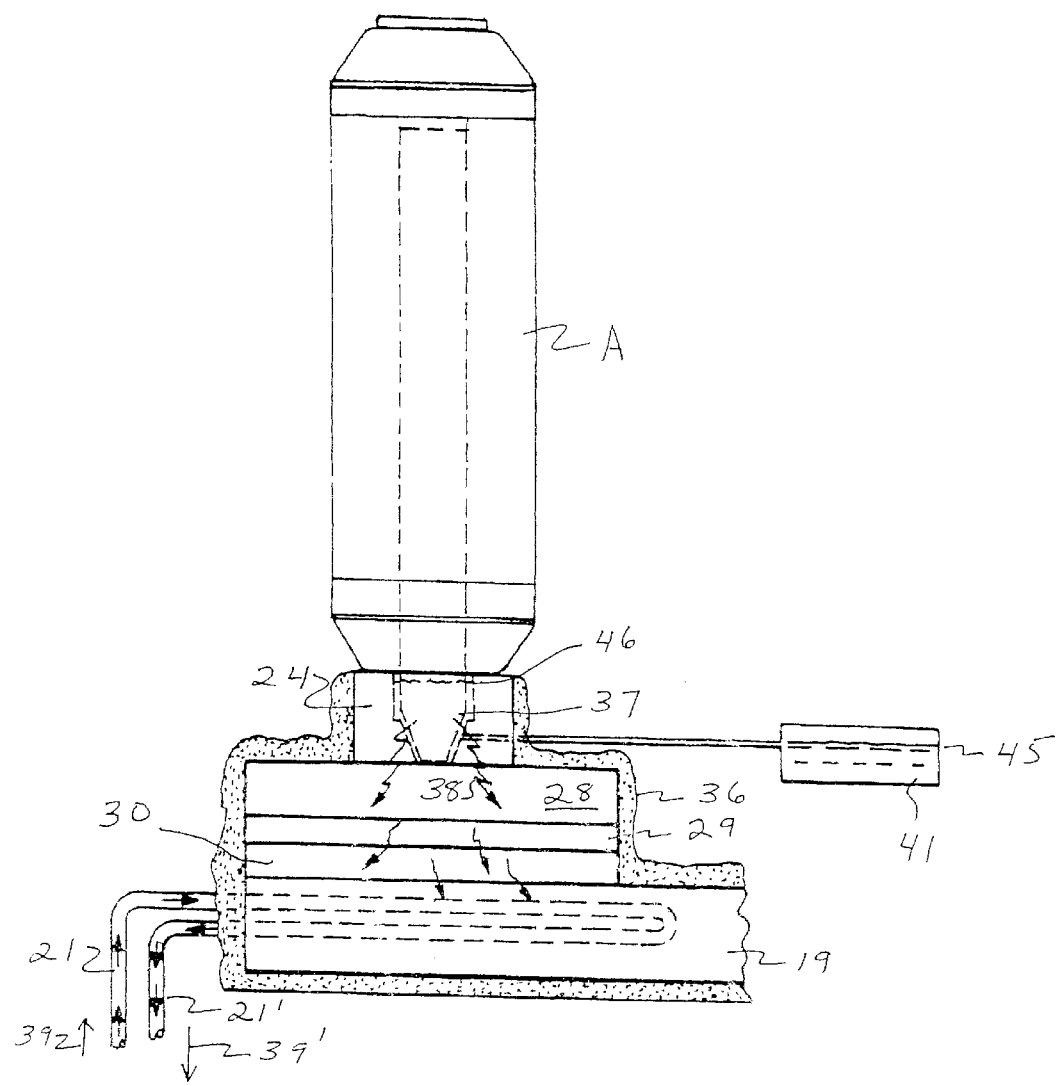
FIG. 4C is a side, partially cut-away view of the preferred device of FIGS. 1 and 2, illustrating the applicator plugged into a charging station socket, and further illustrating the chilling operation of the thermal cooling unit.

Referring to FIGS. 1 and 2 of the drawings, the preferred embodiment of the present invention (currently working via prototype) comprises two primary components, a hand-held applicator A comprising a thermal mass 1 which is insulated 2 along its length, but for an exposed 3 end. The applicator itself has no working components, other than a temperature gage which may be added.

Rather, the thermal mass comprising the applicator is cooled to a cryogenic temperature (−100 degrees C or better) via a separate thermal cooling unit 4, which is configured to removably interface with and extract heat from the thermal mass via a charging station 6 having one or more sockets 5 configured to interface with the exposed 3 end of the applicator, the thermal cooling unit relying upon internal refrigeration component(s) 8 to cool the charging stations, which refrigeration component(s) can be controlled via controls 7 and monitored via display 9.

Continuing with FIGS. 6 and FIGS. 6A-6F, the applicator is passive in operation, relying upon a chilled thermal mass 1 in the illustrated form of a rod of, for example, copper rod (working embodiment having alloy 10100), selected for its high thermal storage capacity and relatively fast thermal conductivity. As shown, the rod has first 10 and second 11 ends, and a length 12 which is insulated by polyurethane foam 13 or the like for resisting atmospheric warming, while providing an area to grasp and manipulate the unit. An exposed portion 14 emanates from the insulation at the first end, which end is tapered 16 to a tip 17. The size and configuration of the thermal mass may vary 16, 16', 16", as well as the taper and tips 17, 17", 17"', respectively, depending upon the anticipated use and associated heat extraction requirements. The exemplary rods shown are 0.5 inches in diameter, about five inches in length. The exemplary tips of the rods forming thermal mass 6B is 0.190 inches, 6D 0.40 inches, and 6F 0.25 inches.

The storage capacity, or quantification of above exemplary thermal mass of the present application is calculated as:

Mass=14.42×10−3 Kg, from 30 deg. C through −100 deg. C, the energy is 721.7 Joules.

Referring to FIGS. 1, 4, 4A, 4B and 4C, the charging station 18 of the thermal cooling unit is primarily cooled by a refrigerator means 20 (in the working embodiment, cascaded Rankine process refrigeration units) having lines 21, 21' configured to provide chilled refrigerant ( about −89 degrees Centigrade) to flow 39, 39' through a cold plate 19 of, for example, copper alloy 10100, which has stacked thereupon a spacer 30 of similar metal, which may have situated thereupon a secondary cooling means comprising a thermoelectric device 29 (for example, a Peltier device by Melcor Corp. of Trenton, N.J., having model number 2SC085065-127-70L), said thermoelectric device having its hot side 33 engaging the spacer 30 and its cold side 34 engaging a base plate 28 of, for example, copper (same alloy as cold plate), so as to further lower the cooling temperature of the unit to about −100 degrees C.

The first and second Rankine refrigeration units utilized in the present, exemplary embodiment of the invention were manufactured by Tecumseh, Brazil, and Embraco, Italy, respectively and were assembled in a cascaded fashion by Scientemp Corporation of Adrian, Mich., 49221, www-.scientemp.com. The units interface in a cascaded fashion wherein there is a high temperature refrigerant, −35 degrees centigrade, interfacing via a welded finned heat exchanger, with a low temperature refrigerant, at about −85 degrees centigrade when at low temperature, providing a combined cooling capacity of 100 watts at said low temperature, where the chilled refrigerant from the second unit flows in a serpentine fashion though the cold plate.

An example of an off-the-shelf cascaded Rankine process refrigeration units would be suitable for the present application could comprise, for example, the LEGACI brand refrigeration system by REVCO TECHNOLOGIES of Asheville, N.C. 28804, www.revco-sci.com. The Ultima II Series line of Ultra-Low Temperature Freezers by REVCO TECHNOLOGIES incorporates the LEGACI brand refrigeration system. An illustration of the Method of operation of the LEGACI brand refrigeration system may be found at http://www.revco-sci.com/pdf/legaci$_{13}$ schematic.pdf; a copy of this schematic, entitled "New Refrigeration Technology" (no date), as well as pages from the REVCO TECHNOLOGIES online catalog at http://222.revco-sci.com/catalog/ult/ult$_{13}$ value.htm captioned "Value Series Ultra-Low Temperature Freezers" are attached to the Information Disclosure Statement filed herewith in the present case, and their contents are incorporated herein by reference.

Situated atop the base plate 28 is an application interface 23 in the form of a socket 24 having a bore 25 formed therein, the bore having a diameter of the thermal mass to be engaged (in this case, a 0.5 inch cylindrical rod), and a taper 26 and bottom 27 formed to engage the taper and tip of the exposed portion of the applicator(s) 35 to be engaged, so that the applicator exposed tip may be plugged into the socket and heat extracted from the thermal mass of the applicator in this manner.

Ideally, thermal grease 32 is situated between each layer conjoining the cold plate, spacer, thermoelectric device, base plate, and socket, and the various components may be held together via fasteners 31 or the like. Ideally, the components forming the charging station are insulated, for example, by a layer of polyurethane foam 36.

Continuing with FIGS. 4C, 5, 5A and 5B, an antifreeze tank 41 is provided adjacent to the charging station to provide a consistent level of antifreeze fluid to each socket 43 to fill between, and prevent air gaps, in the clearance 37 between the applicator exposed end and the socket when conjoined, thereby enhancing heat transfer 38 from the thermal mass of the applicator, through the thermoelectric device (when used) to the cold plate 19. The exemplary reservoir system shown is of a gravity fill 42 type, that is, the level 46 of fluid in the empty socket is maintained to a level equal to the level 45 in the adjacent tank via conduit 44.

Not only does the antifreeze increase the efficiency of transfer from the exposed end of the applicator to the socket (and on to the cold plate), it also prevents moisture condensation on the exposed, chilled portion from the air by providing a coating of antifreeze upon the chilled, exposed end. Purified Ethanol (about 99.9% pure) has been found to provide the best performance to date for use as an antifreeze in this application, although other fluids may be similarly suitable for use at the operating temperature of the present system, which is about −100 degrees Centigrade.

Figure 10:
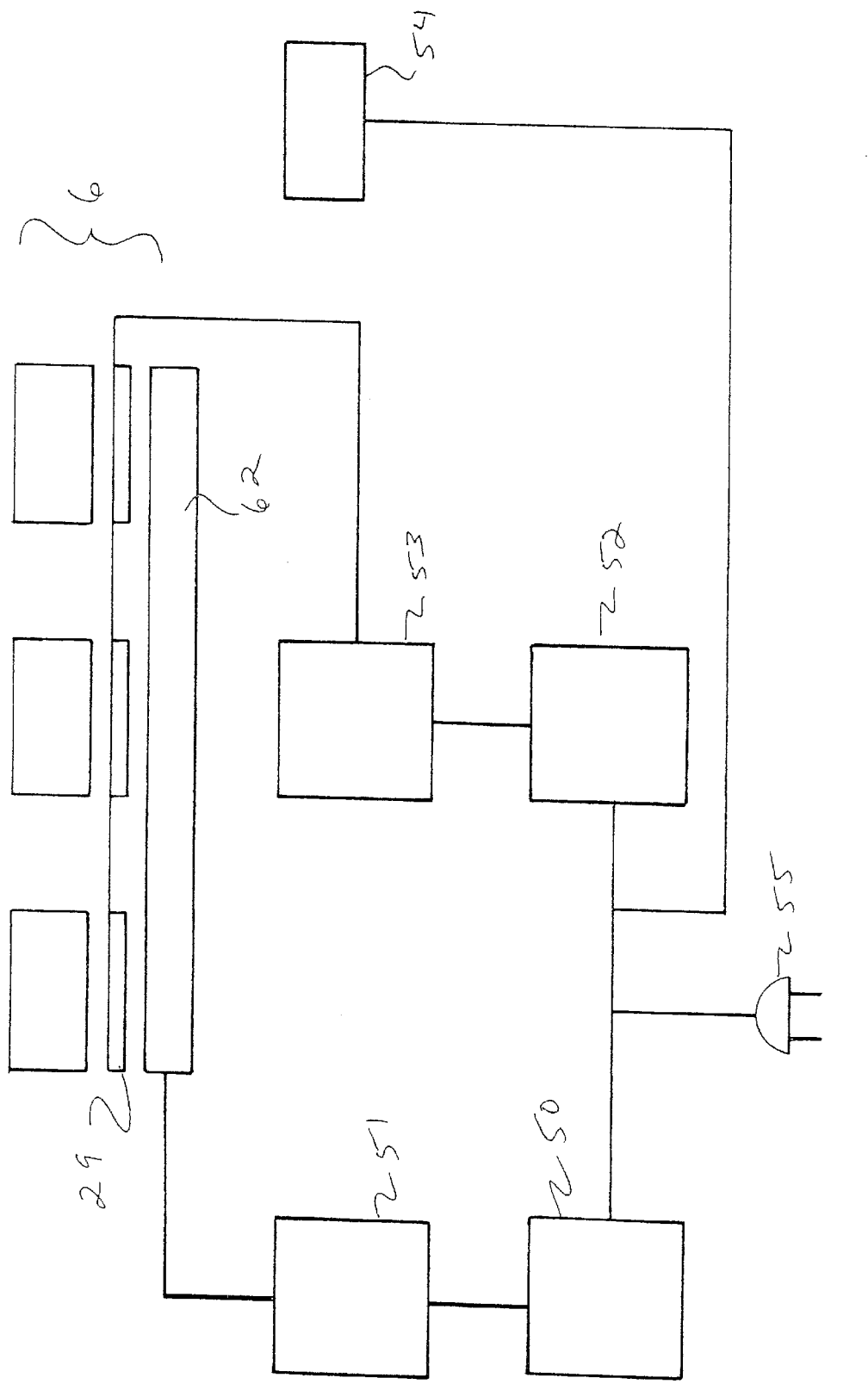
FIG. 10 is a basic block diagram illustrating the various components of the preferred, working cooling unit of the invention of FIG. 1.
Figure 11:
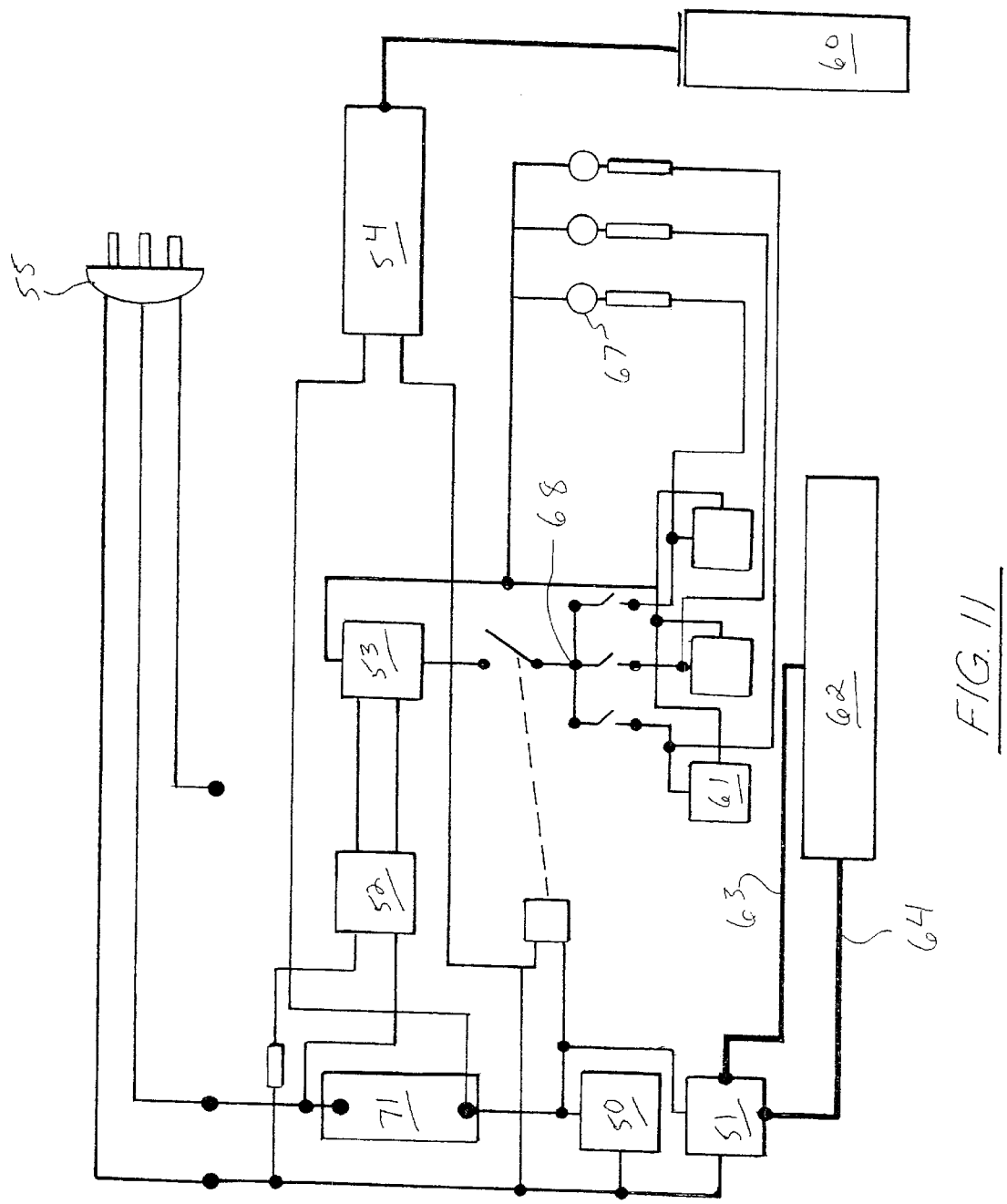
FIG. 11 is a more detailed block diagram of the invention of FIG. 10.

Referring to FIGS. 10 and 11, the present, working embodiment of the present invention utilizes first 50 and second 51 Rankine cycle refrigeration units in cascaded arrangement to bring the cold plate 62 to a temperature of about −89 degrees Centigrade; stacked thermoelectric device(s) 29 further lower the sockets to about −100 degrees, as discussed supra.

The thermoelectric devices in the present embodiment are powered by a battery 53 which is charged via charger 52, powered by line 55. A temperature indicator 54 monitors the temperature of the socket(s) engaging the applicator 60, displaying the temperature and/or status of same. Refrigeration units 50, 51 (which circulate chilled refrigerant to the cold plate via lines 63, 64) are configured to provide chilled refrigerant to the cold plate at about 89 degrees Centigrade, and generally would not require thermostatic control, chilling the cold plate, as well as pulling heat from the thermoelectric device and socket to about −89 degrees Centigrade, although the temperature can vary depending upon the refrigeration system, refrigerant, and operational and environmental criteria. Thermoelectric device(s) 29, 61, are controlled via relay 68, which energizes the thermoelectric devices when the refrigeration units 50, 51 (i.e., compressors) are operating to further chill the socket, bringing the temperature of the socket down to about −100 degrees Centigrade, as indicated above.

LED's 67 display status for each applicator interface/socket forming the charging station. A circuit breaker 71 prevents overloading of the power supply, or in shuts down power in the event of equipment malfunction or shorting.

Continuing with FIGS. 1, 4C, 3, and FIGS. 3A–3F, in use, an applicator A is selected by a user taking into consideration its size and thermal mass, depending upon the operation involved. The selected applicator A is plugged into a socket suitable for receiving its exposed end at the charging station of the thermal cooling unit. The socket, cooled via the underlying cold plate and thermoelectric device (when used), draws heat 38 from the thermal mass of the applicator until equilibrium is reached, at about −100 degrees Centigrade. Upon reaching the predetermined temperature, the thermal cooling unit indicates via display 9 or other visual or auditory signal that the applicator has been sufficiently chilled for the determined use. To this end, the temperature monitoring/control circuitry for the thermal cooling unit may be pre-programmed to control, monitor, and maintain the applicator at a variety of predetermined temperatures for different operations.

Once chilled, the applicator may be grasped by the user 79 and removed from the socket. A layer of antifreeze remains on the exposed, chilled tip of the thermal mass, preventing the formation of ice crystals on same.

The exposed tip may then be directly applied to the area to be treated, or ideally an applicator tip 75 is selected and applied 80 to the exposed tip, the applicator tip having a socket formed of a layer 77' of thermally conductive material configured to closely engage the exposed end of the thermal mass, the inner layer facilitating the transfer of heat from the applicator portion 78 to the thermal mass; an insulated portion 77 forms an outer layer about the inner layer 77' (FIG. 8B) to prevent unnecessary heat absorption from the air. Antifreeze remaining on the exposed tip forms an ideal interface between the exterior tip of the applicator and the inner layer of the applicator tip.

A locking mechanism 84 such as a latch (shown) or the like may be provided to removably retain 83 the applicator tip in place. Once installed, the tip is given a chance to have the heat drawn therefrom by the super-chilled thermal mass, and the tip then applied 80' to the desired treatment area 81 of the tissue 82 and held in place, so as to communicate with 85 and draw heat from 86 the tissue, cryosurgical freezing and thereby ablating 87 same, within an acceptable area 88 and depth 89.

If the applicator tip were to freeze to the tissue so as to prevent removal of same, the applicator can be quickly unlatched 90 or otherwise removed 91 from the applicator tip and retracted 93; as said tip has little thermal mass, it quickly heats to room temperature, and can thereafter easily be removed 92. This is particularly useful for treating moist tissues, such as in the mouth and gynecological, rectal, or other mucous membrane areas.

Figure 9:
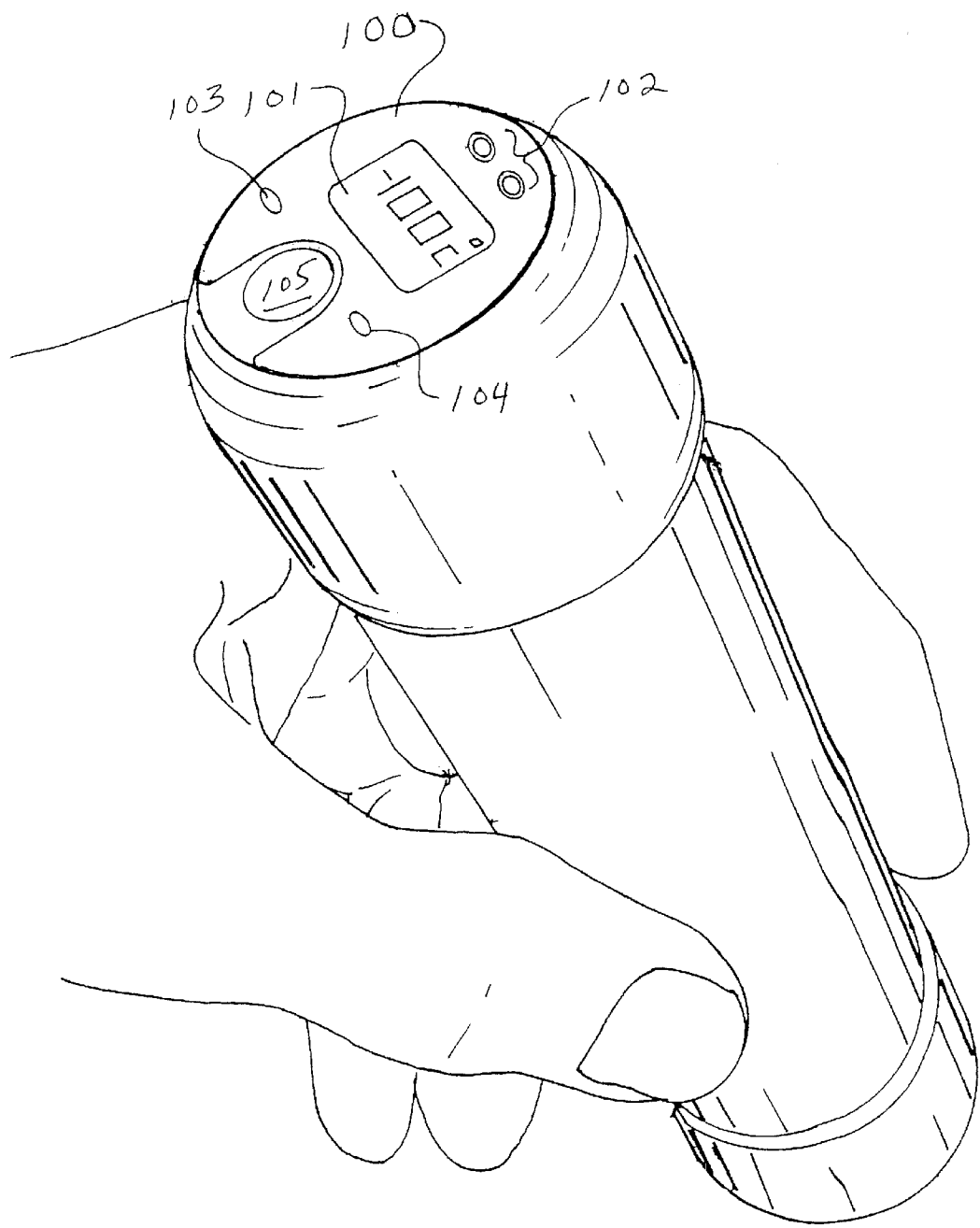
FIG. 9 is an isometric view of the applicator of FIGS. 2 or 7 having temperature indicator means situated thereupon.

Continuing with FIG. 9, a temperature indicator unit 100 having sensors communicating with the thermal mass forming the core of the applicator, may be provided for consultation during use. The unit 100 may include a display 101, controls 102 for indicating alarms, timer, or the like, LED red and/or green indicators 103, 104, and an audible alarm 105 may be provided to give status and feedback as to operating criteria and when to re-chill the unit.

Referring to FIGS. 8, 8A and 8B, the applicator tip 75 includes an applicator portion 115 which can vary depending upon the operation, the said application portion configured to best conform with the anatomy of the tissue to which it is applied; several various exemplary applicator tips are shown in FIGS. 8C–8K, said configurations based upon existing designs for other devices.

FIGS. 7 and 7A illustrate views of an alternative design for an applicator, wherein the foam insulation surrounding the thermal mass 119 has been replaced with a vacuum insulation housing 116, comprising a vacuum jacket 118 having an outer grasping surface 117, revealing at an exposed end 120 of the thermal mass for communication with an application tip 121 thereto. The implementation and operation of the system is otherwise the same as the above embodiment(s).

Figure 12:
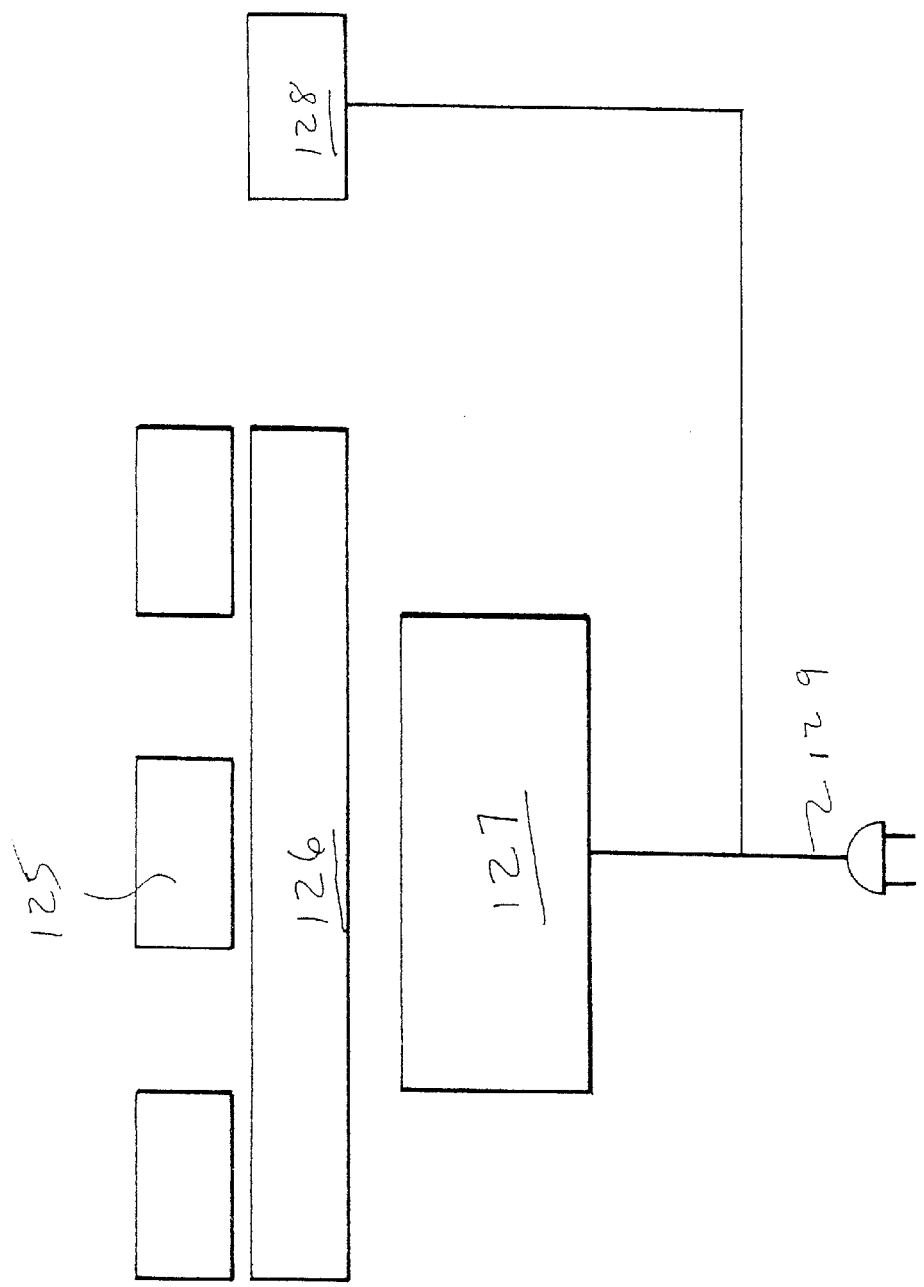
FIG. 12 is a block diagram of an alternative embodiment of a cooling unit of the present invention, utilizing a Stirling cycle refrigeration unit.
Figure 13:
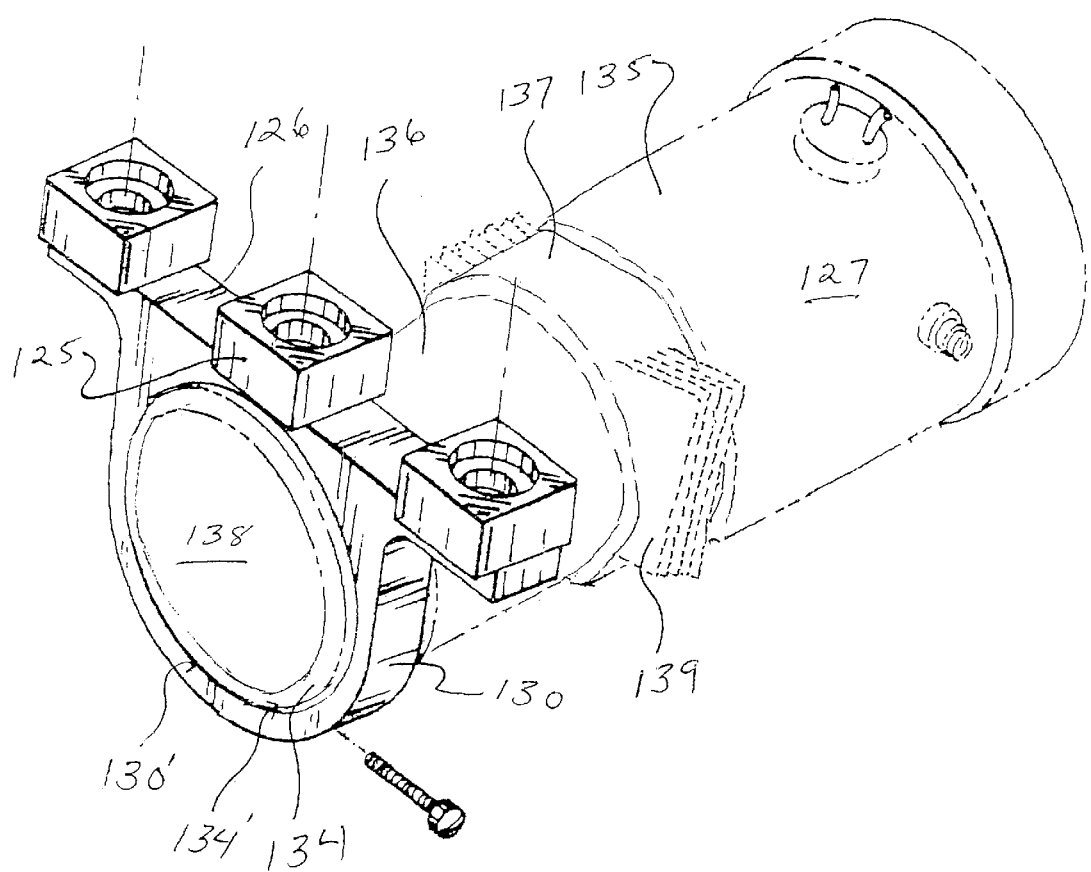
FIG. 13 is an isometric view of a radial interface configured to engage the Stirling cycle refrigeration unit of FIG. 12, the figure further illustrating a cool plate integrated therein engaging three sockets for receiving the exposed ends of three applicators, respectively.

FIGS. 12 and 13 illustrate an alternative refrigeration means for the thermal cooling unit of the present invention, wherein a Free Piston Stirling Cooler 127, Model number M100B as provided by Global Cooling B.V. having U.S. Offices in Athens, Ohio and an Internet Web Site at www.globalcooling.com, is utilized to cool the cold plate and associated sockets forming the charging station. Detailed operation of a Stirling Cooler like the M100B is provided in the document "Design and Testing of a 40 W Free-Piston Stirling Cycle Cooling Unit" by Berchowitz, McEntee and Welty, 20th Int'l Congress of Refrigeration, IIR/IIF, Sidney 1999, the contents of which are incorporated herein by reference.

The M100B Stirling Cooler by Global Cooling B.V. utilizes non-ozone depleting Helium as the refrigerant, readily reaches temperatures to below –100 degrees Centigrade (therefore does not require a separate thermoelectric device for a boost as with the first embodiment), is smaller and utilizes much less energy to operate than the first embodiment. However, the unit is expensive to purchase at this time, although it is anticipated that the cost will come down with mass production.

As shown, the cooler 127 has two primary sections, an electromagnetically actuated linear motor section 135, and a regenerator section 136, which has situated therein a displacer piston driven by said linear motor. The regenerator section has first and second ends, forming "cold" 138 and "hot" 137 ends of the unit, respectively.

A finned heat sink 139 is provided at the "hot" end to displace heat, while a ring 134 of thermally conductive, thermal mass material such as copper is provided about the "cold" end.

In the present invention, the cold plate 126 communicates with a thermal engagement ring 130 having an inner diameter 130' configured to engage the outer diameter 134' of the ring 134; as shown, three base plates having sockets 125 for engaging the applicators are situated upon the cold plate. In operation, heat is pulled via the "cold" end of the Stirling cooler, via the thermally conductive material from the cold plate, associated base plates, sockets, and engaged applicators, chilling same. The temperature is controlled via temperature sensor/controller/display unit 128.

The advantage of this alternative embodiment is that it is much smaller, simpler, and more energy efficient than the first embodiment, while performing similar cryogenic cooling capabilities; however, due to difficulties in production at the present, the Stirling cooler costs much more at this time than more conventional refrigeration units, although the price may drop in the future, as earlier indicated. Still another cooling means may be found in the "pulse tube cryo cooler" developed by government scientists at the National Institute of Standards and Technology.

To summarize, a method of cryosurgically treating selected tissue on a patient could comprise, for example, the steps of:

a) providing a cryogenic apparatus, comprising:
an applicator, comprising:
a thermal mass having first and second ends, said thermal mass at least partially insulated to form a probe which may be held by a user;
a thermal cooling unit, comprising:
a charging station having a socket configured to removably engage said thermal mass of said applicator; and
cooling means for cooling said socket;
said applicator formed to engage said socket of said charging station so as to allow said cooling means to remove heat from said thermal mass so as to cryogenically cool same, said applicator further being separable from said socket, such that said chilled thermal mass may be utilized to extract heat from an application area;

b. engaging said applicator to said charging station such that said socket engages said thermal mass of said applicator;

c. allowing said cooling means to remove heat from said thermal mass via said socket, to –40 degrees centigrade or cooler;

d. removing said applicator from said charging station;

e. placing said thermal mass in the vicinity of the selected tissue, and utilizing said thermal mass to freeze the selected tissue to a temperature of –40 degrees Centigrade or cooler until the selected tissue is ablated;

f. removing said thermal mass from the selected tissue.

Figure 14:
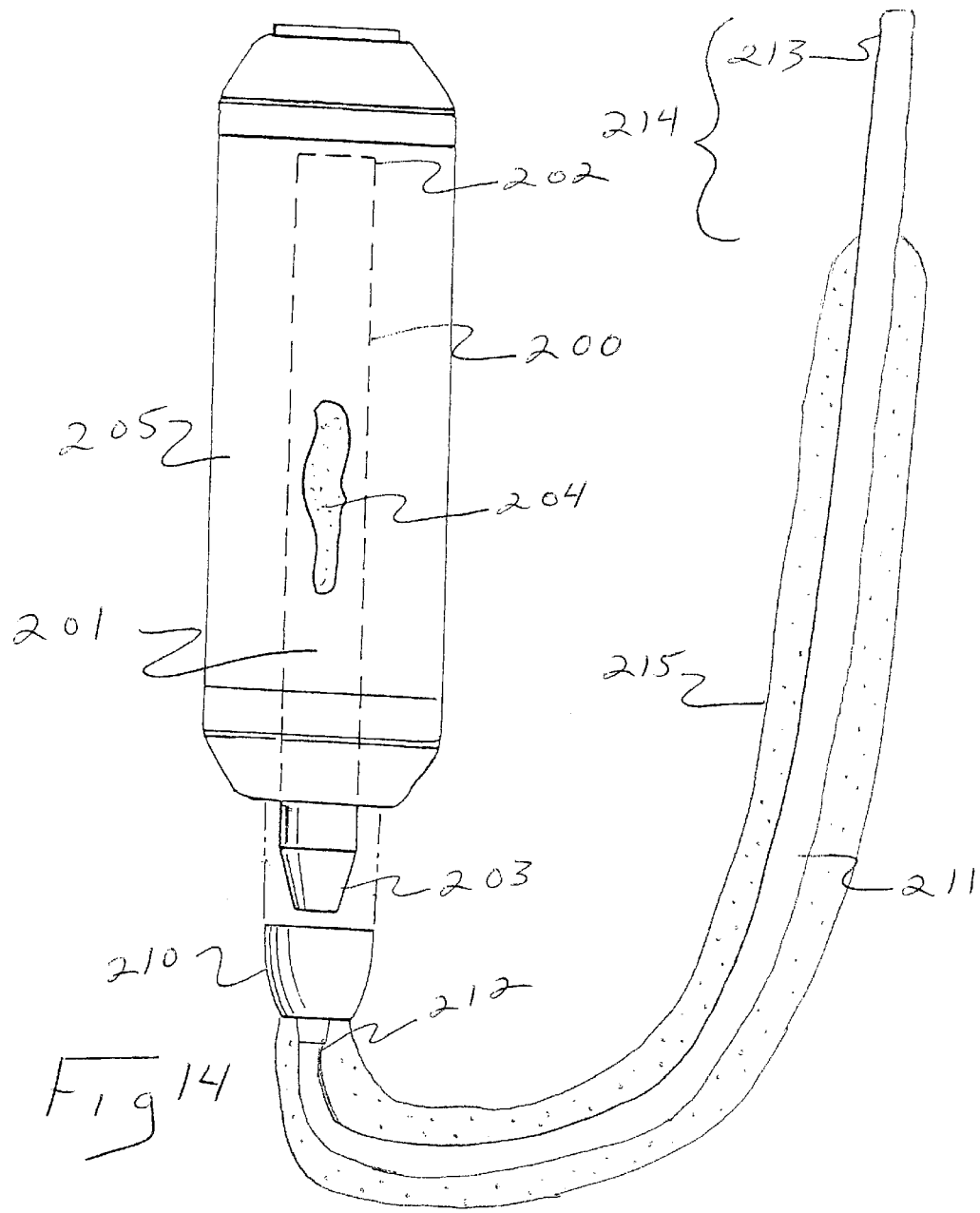
FIG. 14 is a side, partially cut-away view of an alternative application embodiment of the present invention, illustrating an application tip in the form of an insulated heat pipe having first and second ends, the first end configured to engage the tip of the thermal mass, the second end providing an application tip for treating remote tissue in a patient.

Continuing with FIG. 14 of the drawings, an alternative thermal mass 200 of the present invention is shown comprising a container 201 of thermally conductive material such as copper or the like having first 202 and second ends 202 and a sealed hollow interior 203 containing a thermal storage material 204, preferably a cryogenic phase change material such as ethyl acetate or butyl acetate, which is fluid at room temperature but freezes solid at around 80 degrees Centigrade. The benefit of utilizing this material is that, when the temperature of the chilled unit rises to the phase change temperature (for example, 80 degrees centigrade), the phase change from solid to liquid results in dissipation of heat energy, resulting in a slowing of the warming of the material, and the continued ability to utilize the material at cryogenic temperatures during an operation. This unit would be chilled in a thermal cooling unit as with the preferred embodiment of the present invention, has an exterior body configuration insulated 205 with thermal insulation, the second end 202 of the unit preferably exposed and configured to interface with the socket of the charging station, as well as forming an application tip or interface for an appliance, treatment tip, or the like.

FIG. 14 also illustrates an appliance 210 configured to provide treatment to remote internal or otherwise remotely accessible areas of the body of a patient, such as in endocervical cryogenic ablation treatment, utilizing a heat pipe 211 having first 212 and second 213 ends, the first end of the heat pipe configured to engage the second end 203 or exposed tip of the thermal mass, the second end of the heat pipe ideally providing an exposed area 214 configured to treat the target area of a patient (for example, the cervix) for cryogenic treatment of same. The length of the heat pipe may be insulated 215, with the treatment end (the second end) exposed as discussed above, or alternatively configured to engage a specifically configured thermal application tip such as, for example those illustrated in FIGS. 8A–8K, or other cryogenic application probes or tips, typically formed from thermally conductive material.

Exemplary measurements:
Heat pipe diameter 5 mm
Heat pipe length 300 mm
Thermal mass diameter 10 mm In use, the thermal mass would be chilled as discussed above utilizing the charging station. Once sufficiently cooled to the desired temperature, an appliance 210 is affixed to the thermal mass, and the treatment end of the appliance directed to the area to be treated on or in the patient. Heat energy from the treatment area would be drawn by the heat pipe through contact with the tissue to the cryogenically chilled thermal mass, so as to freeze the treatment area. Use of the heat pipe thereby avoids the need to have the thermal mass in the immediate vicinity of the area to be treated, allowing for the use of a more slender, flexible treatment tool for specialized cryosurgical operations. The outer portion of the heat sink and/or heat pipe may be silver coated to facilitate more efficient thermal transfer.

In still another alternative configuration of the present invention, the heat pipe could be joined to the second end of the thermal mass via soldering or other means; in such an embodiment, the first end of the heat pipe ideally could be configured to engage the charging station for heat removal. In this version of the invention, the heat pipe would be permanently affixed to the thermal mass.

In conclusion, the present embodiment provides a practical, cost effective, safer, and simpler system to train, implement, and maintain than the prior art, providing a light weight, passive, chilled thermal mass configured for cryosurgical applications, and a thermal cooling unit which effectively removes heat from the applicator(s) for continuous use in a medical office or the like. The application tips, being readily interchangeable in size, along with the applicators and their possibly diverse thermal masses, can be chosen specifically for the desired procedure, providing the perfect cryosurgical tool for a variety of operations. The application tip associated with the heat pipe may include resistance or other heating means, such as an electric film heater for providing immediate thawing of the treatment portion of the heat pipe or applicator tip to facilitate thawing of a frozen joint between the patient tissue and heat pipe.

In use, the thermal mass is utilized as a heat sink which is directly or indirectly applied to the treatment area. The chilled thermal mass must have sufficient mass to form a heat sink which is capable of removing sufficient heat from the tissue at the start of cryo surgery, for example, 5–15 watts, although the true amount can vary substantially depending upon the procedure.

The interface connection between the appliance 210 and the second end of the thermal mass, like the earlier discussion of the applicator tips in FIGS. 8A–8K, maintains a removable connection even at cryogenic temperatures when the antifreeze bath is utilized as part of the charger station and associated chilling operation, as a layer of antifreeze remains on the second end of the thermal mass, and forms a liquid thermal interface between the thermal mass and the appliance, and associated heat pipe.

The invention embodiments herein described are done so in detail for exemplary purposes only, and may be subject to many different variations in design, structure, application and operation methodology. Thus, the detailed disclosures therein should be interpreted in an illustrative, exemplary manner, and not in a limited sense.

What is claimed is:

1. A cryogenic apparatus, comprising:
    an applicator, comprising:
        a thermal mass having first and second ends;
    a thermal cooling unit, comprising:
        a charging station having a socket configured to removably engage said thermal mass of said applicator;
        a quantity of thermally conductive fluid situated in said socket; and
        cooling means for cooling said socket;
    said applicator formed to engage said socket of said charging station in conjunction with said thermally conductive fluid situated in said socket so as to allow said cooling means to remove heat from said thermal mass to cryogenically cool same, said applicator further being separable from said socket, such that said chilled thermal mass may be utilized to extract heat from an application area.

2. The cryogenic apparatus of claim 1, wherein said charging station further comprises a cold plate.

3. The cryogenic apparatus of claim 2, wherein said cooling means comprises first and second, cascaded Rankine cycle refrigeration units to cool said cold plate.

4. The cryogenic apparatus of claim 3, wherein said cooling means further comprises a thermoelectric device having a hot side and a cold side, said hot side communicating with said cold plate, said cold side communicating with said socket.

5. The cryogenic apparatus of claim 1, wherein said charging station comprises a cold plate communicating with said socket, and wherein said cooling means comprises a Stirling cycle cooler having a hot end and a cold end, said cold end engaging communicating with said cold plate.

6. The cryogenic apparatus of claim 1, wherein there is further provided an application tip formed to removably engage said chilled thermal mass, said application tip configured to engage an application area to draw heat therefrom.

7. The cryogenic apparatus of claim 6, wherein said application tip comprises a heat pipe having first and second ends, said first end of said heat pipe configured to engage said chilled thermal mass, said second end of said heat pipe configured to engage a treatment area on a patient.

8. The cryogenic apparatus of claim 7, wherein heat pipe has a length, and wherein a portion of said length of said heat pipe is insulated.

9. The cryogenic apparatus of claim 8, wherein there is provided an applicator tip configured to removeably engage said second end of said heat pipe, said applicator tip configured to engage treatment area on a patient.

10. The cryogenic apparatus of claim 5, wherein there is further provided an application tip formed to removably engage said chilled thermal mass, said application tip configured to engage an application area to draw heat therefrom.

11. The cryogenic apparatus of claim 1, wherein said applicator further includes temperature indicator means for indicating the temperature of said thermal mass.

12. The cryogenic apparatus of claim 1, wherein said thermal mass contains phase change material.

13. The cryogenic apparatus of claim 2, wherein said thermally conductive fluid comprises antifreeze fluid, and wherein there is further provided an antifreeze dispenser for dispensing said antifreeze fluid into said socket, so as to maintain a predetermined level of antifreeze fluid in said socket.

14. The cryogenic apparatus of claim 13, wherein said antifreeze fluid comprises ethanol.

15. The cryogenic apparatus of claim 14, wherein said thermal mass comprises a rod of copper.

16. The cryogenic apparatus of claim 1, wherein there is further provided a heat pipe having first and second ends, said first end of said heat pipe affixed to said second end of said thermal mass, said second end of said heat pipe configured to extract heat from a treatment area.

17. A method of cryogenically cooling a treatment area, comprising the steps of:
    a) providing a cryogenic apparatus, comprising:
        an applicator, comprising:
            a thermal mass having first and second ends, said thermal mass at least partially insulated to form a probe which may be held by a user;
        a thermal cooling unit, comprising:
            a charging station having a socket configured to removably engage said thermal mass of said applicator; and
            cooling means for cooling said socket;
        said applicator formed to engage said socket of said charging station so as to allow said cooling means to remove heat from said thermal mass so as to cryogenically cool same, said applicator further being separable from said socket, such that said chilled thermal mass may be utilized to extract heat from an application area;
b. placing a quantity of thermally conductive fluid in said socket of said charging station, and engaging said applicator to said charging station such that said socket engages said thermal mass of said applicator utilizing said thermally conductive fluid;
c. allowing said cooling means to remove heat from said thermal mass via said socket;
d. removing said applicator from said charging station;
e. utilizing said thermal mass to cool the treatment area;
f. removing said thermal mass from the treatment area.

18. A method of cryosurgically treating selected tissue on a patient, comprising the steps of:
a) providing a cryogenic apparatus, comprising:
an applicator, comprising:
a thermal mass having first and second ends, said thermal mass at least partially insulated to form a probe which may be held by a user, said first end of said thermal mass having an application tip;
a tip cover configured to removeably engage said application tip, said tip cover formed of a thermally conductive material;
a thermal cooling unit, comprising:
a charging station having a socket configured to removably engage said thermal mass of said applicator; and
cooling means for cooling said socket;
said applicator formed to engage said socket of said charging station so as to allow said cooling means to remove heat from said thermal mass so as to cryogenically cool same, said applicator further being separable from said socket, such that said chilled thermal mass may be utilized to extract heat from an application area;
b. engaging said applicator to said charging station such that said socket engages said thermal mass of said applicator;
c. allowing said cooling means to remove heat from said thermal mass via said socket;
d. applying said tip cover to interface with said application tip of said thermal mass;
e. placing said application tip having said tip cover thereon in the vicinity of the selected tissue, and utilizing said thermal mass to freeze the selected tissue, via said tip cover;
f. removing said thermal mass from the vicinity of the selected tissue, while allowing said tip cover to remain in the vicinity of the selected tissue, providing a removed tip cover;
g. allowing said removed tip cover to warm due to contact with ambient air and the selected tissue; and
h. removing said removed tip cover from said selected tissue.

19. The method of claim 18, wherein step "d" further includes the step of providing a quantity of thermal conductive fluid between said application tip and said tip cover, so as to form a liquid thermal interface between said application tip and said tip cover.

20. The method of claim 19, wherein in step "f" said tip cover is frozen to the selected tissue so as to adhere to said tissue, and wherein in step "g" said removed tip cover is allowed to thaw so as to no longer adhere to said tissue.

21. The method of claim 18, wherein step "C" further includes the step of engaging the first end of a heat pipe to said thermal mass, and wherein the tip cover of step "D" is applied to the second end of said heat pipe, so as to allow said heat pipe to transfer heat from said tip cover to said thermal mass.

22. A method of Cryosurgery, comprising the steps of:
a. providing a thermal mass having an applicator tip;
b. placing said applicator tip into a liquid bath of chilled thermally conductive fluid so as to chill said applicator tip and said thermal mass, removing said applicator tip from said liquid bath, providing a chilled applicator tip having a layer of thermally conductive fluid thereupon;
c. extracting heat from a treatment area utilizing said chilled applicator tip;
d. allowing said chilled thermal mass to extract heat from said treatment area so as to freeze and ablate said treatment area, providing a frozen treatment area; while
e. allowing said layer of thermally conductive fluid on said applicator tip to prevent said frozen treatment area from adhering from said applicator tip when said applicator tip is removed from said frozen treatment area.

23. A cryogenic treatment system, comprising:
a first Rankine cycle refrigerator unit providing chilled refrigerant;
a second Rankine cycle refrigerator unit cascaded with said first Rankine cycle refrigerator unit, so as to further chill said chilled refrigerant, providing cryogenically chilled refrigerant;
a cold plate formed to interface with said cryogenically chilled refrigerant, providing a cryogenically chilled cold plate;
a thermoelectric device having hot and cold sides, said hot side of said thermoelectric device formed to interface with said cold plate, providing a cryogenically chilled thermoelectric device,
a socket in communication with said cold side of said thermoelectric device, so as to provide a cryogenically chilled socket having a lower temperature than said cryogenically chilled cold plate; and
a thermal mass configured to engage said socket for cooling said thermal mass, providing a cooled thermal mass, wherein said cooled thermal mass may be removed from said socket and applied to a treatment area.

24. A cryogenic treatment system, comprising:
a thermal mass having first and second ends, said thermal mass at least partially insulated so as to be held by a user;
a thermal cooling unit, comprising:
a charging station having a socket configured to removably engage said thermal mass; and
cooling means for cooling said socket;
said thermal mass formed to engage said socket of said charging station so as to allow said cooling means to remove heat from said thermal mass to cryogenically cool same, said thermal mass further being separable from said socket; and
a heat pipe having first and second ends, said first end of said heat pipe configured to engage to said thermal mass, said second end of said heat pipe configured to extract heat from a treatment area.

* * * * *